United States Patent
Nazarian et al.

(10) Patent No.: US 12,263,312 B2
(45) Date of Patent: Apr. 1, 2025

(54) FACIAL WEARABLE DEVICE AND METHODS FOR PROVIDING EXTERNAL STIMULI USING THE SAME

(71) Applicant: Therabody, Inc., Los Angeles, CA (US)

(72) Inventors: Benjamin Nazarian, Los Angeles, CA (US); Jason Wersland, Los Angeles, CA (US); Jaime Sanchez Solana, Los Angeles, CA (US); Eduardo Merino, Los Angeles, CA (US); Mandar Deshmukh, Los Angeles, CA (US); Timothy Roberts, Los Angeles, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 18/484,677

(22) Filed: Oct. 11, 2023

(65) Prior Publication Data

US 2024/0033466 A1 Feb. 1, 2024

Related U.S. Application Data

(62) Division of application No. 17/933,419, filed on Sep. 19, 2022, now Pat. No. 11,819,625.

(Continued)

(51) Int. Cl.
*A61M 21/02* (2006.01)
*A61M 21/00* (2006.01)
*A61N 1/36* (2006.01)

(52) U.S. Cl.
CPC ......... *A61M 21/02* (2013.01); *A61N 1/36028* (2013.01); *A61N 1/36031* (2017.08);
(Continued)

(58) Field of Classification Search
CPC .......... A61M 21/02; A61M 2021/0022; A61M 2021/0066; A61M 2205/3303;
(Continued)

(56) References Cited

U.S. PATENT DOCUMENTS 327,438 A 9/1885 Fuller
1,545,027 A 7/1925 Ashlock
(Continued)

FOREIGN PATENT DOCUMENTS

CA 107532 S 9/2005
CA 126241 S 6/2009
(Continued)

OTHER PUBLICATIONS

English Translation of CN215839897 to Wu Jian-Feng, Feb. 18, 2022 (Year: 2022).*

(Continued)

*Primary Examiner* — Sunita Reddy
(74) *Attorney, Agent, or Firm* — Sterne, Kessler, Goldstein & Fox P.L.L.C.

(57) ABSTRACT

A facial wearable device for providing external stimuli to a user comprises a foldable frame, a flexible layer, an airbag layer, a plurality of heating pads, a plurality of vibrating motors, and a sensor. The flexible layer may couple to a proximal side of the foldable frame and be configured to couple to a facial area of the user. The airbag layer may be disposed between the foldable frame and the flexible layer and comprise a plurality of inflatable bladders configured to provide pressure to the facial area of the user. The plurality of heating pads may couple to the flexible layer and be configured to provide heat to the facial area of the user. The plurality of vibrating motors may couple to the flexible layer and be configured to provide vibration to the facial area of the user. The sensor may couple to the flexible layer and be (Continued)

configured to detect biometric data of the user. At least one of the plurality of inflatable bladders, the plurality of heating pads, and the plurality of vibrating motors may be controlled based on the biometric data.

15 Claims, 17 Drawing Sheets

Related U.S. Application Data

(60) Provisional application No. 63/335,540, filed on Apr. 27, 2022.

(52) U.S. Cl.
CPC ........... *A61M 2021/0022* (2013.01); *A61M 2021/0066* (2013.01); *A61M 2205/3303* (2013.01); *A61M 2205/3561* (2013.01); *A61M 2205/507* (2013.01); *A61M 2210/0606* (2013.01)

(58) Field of Classification Search
CPC .... A61M 2205/3561; A61M 2205/507; A61M 2210/0606; A61N 1/36028; A61N 1/36031
USPC ...................................................... 600/26–28
See application file for complete search history.

(56) References Cited

U.S. PATENT DOCUMENTS

| | | |
|---|---|---|
| 2,191,937 A | 2/1940 | Low |
| D143,678 S | 1/1946 | Snyder et al. |
| 2,987,334 A | 6/1961 | Wendling |
| 3,705,579 A | 12/1972 | Morini et al. |
| D230,522 S | 2/1974 | Rothman |
| D242,666 S | 12/1976 | Smith |
| 4,046,142 A | 9/1977 | Whitney |
| 4,175,297 A | 11/1979 | Robbins et al. |
| D274,438 S | 6/1984 | Angerman et al. |
| D293,504 S | 1/1988 | Specht et al. |
| D308,980 S | 7/1990 | McGee |
| D314,001 S | 1/1991 | Nussbickl |
| D322,795 S | 12/1991 | Dianitsch |
| 5,103,809 A | 4/1992 | DeLuca et al. |
| D351,850 S | 10/1994 | Bolle |
| D352,726 S | 11/1994 | Bolle |
| D439,984 S | 4/2001 | Thach |
| 6,823,762 B2 | 11/2004 | Hu |
| D515,615 S | 2/2006 | Fecteau et al. |
| D519,147 S | 4/2006 | Moritz et al. |
| D550,750 S | 9/2007 | Chiang |
| D556,812 S | 12/2007 | Wang-Lee |
| D569,413 S | 5/2008 | Wong |
| 7,431,706 B2 | 10/2008 | Louis |
| D591,786 S | 5/2009 | Wang |
| D629,034 S | 12/2010 | McNeal et al. |
| D629,035 S | 12/2010 | Moritz et al. |
| 7,927,259 B1 | 4/2011 | Rix |
| 7,927,294 B2 | 4/2011 | Kamimura et al. |
| D649,577 S | 11/2011 | Goodman et al. |
| D653,695 S | 2/2012 | Tobia |
| D657,812 S | 4/2012 | Li |
| D659,644 S | 5/2012 | Gretz |
| D681,283 S | 4/2013 | Wang Lee |
| 8,473,045 B2 | 6/2013 | Terada et al. |
| D687,479 S | 8/2013 | Moritz et al. |
| D687,881 S | 8/2013 | Ginther et al. |
| D695,335 S | 12/2013 | Goodman et al. |
| D704,249 S | 5/2014 | Orzeck |
| 8,777,881 B2 | 7/2014 | Tsai |
| D711,961 S | 8/2014 | Arnette |
| D714,378 S | 9/2014 | Sandor |
| D716,364 S | 10/2014 | Chow et al. |
| D725,175 S | 3/2015 | Wang-Lee |
| D756,180 S | 5/2016 | Chen |
| D761,344 S | 7/2016 | Chen |
| D765,758 S | 9/2016 | Li |
| D765,759 S | 9/2016 | Li |
| D769,350 S | 10/2016 | Orzeck et al. |
| D781,288 S | 3/2017 | Park et al. |
| D784,441 S | 4/2017 | Garfias |
| D785,699 S | 5/2017 | Chen |
| D809,517 S | 2/2018 | Sakata et al. |
| 9,889,066 B2 | 2/2018 | Danby et al. |
| D817,732 S | 5/2018 | Rettler |
| D818,031 S | 5/2018 | Garfias |
| D820,258 S | 6/2018 | Maw et al. |
| D829,810 S | 10/2018 | Nellestam |
| D834,755 S | 11/2018 | Schempp |
| D837,395 S | 1/2019 | Gan |
| D868,878 S | 12/2019 | Langenwalter et al. |
| D895,830 S | 9/2020 | Nakamura |
| D899,502 S | 10/2020 | Liu |
| D900,435 S | 11/2020 | Huang et al. |
| D901,016 S | 11/2020 | Park et al. |
| D903,748 S | 12/2020 | Zhang |
| D906,406 S | 12/2020 | Lee et al. |
| D906,407 S | 12/2020 | Kim et al. |
| 10,881,849 B2 | 1/2021 | Pisarev et al. |
| D909,457 S | 2/2021 | Liang |
| D909,459 S | 2/2021 | Liang |
| D919,696 S | 5/2021 | Dong |
| D922,472 S | 6/2021 | Liang |
| D929,991 S | 9/2021 | Keller et al. |
| D944,885 S | 3/2022 | Choi et al. |
| 11,478,606 B1 | 10/2022 | English et al. |
| D975,090 S | 1/2023 | Deshmukh et al. |
| D978,232 S | 2/2023 | Deshmukh et al. |
| 2004/0044384 A1 | 3/2004 | Leber et al. |
| 2004/0237969 A1 | 12/2004 | Fuller |
| 2005/0146353 A1 | 7/2005 | Schwebel |
| 2006/0135890 A1 | 6/2006 | Tsai |
| 2006/0258930 A1 | 11/2006 | Wu et al. |
| 2009/0077749 A1 | 3/2009 | Roleder et al. |
| 2009/0216070 A1 | 8/2009 | Hunt et al. |
| 2013/0218197 A1 | 8/2013 | Tarumi |
| 2014/0316309 A1* | 10/2014 | Seo ............... A61H 23/02 601/46 |
| 2015/0190607 A1 | 7/2015 | Sugio et al. |
| 2016/0367425 A1 | 12/2016 | Wersland |
| 2016/0374886 A1 | 12/2016 | Wyatt et al. |
| 2017/0042754 A1 | 2/2017 | Fowers et al. |
| 2017/0131553 A1 | 5/2017 | Pletenetskyy et al. |
| 2017/0246076 A1 | 8/2017 | Miller et al. |
| 2017/0252534 A1 | 9/2017 | Nofzinger |
| 2017/0304145 A1 | 10/2017 | Pepe |
| 2017/0312476 A1* | 11/2017 | Woo ............... A61M 21/02 |
| 2017/0340270 A1 | 11/2017 | Ganesh |
| 2018/0099143 A1 | 4/2018 | Kim et al. |
| 2018/0141188 A1 | 5/2018 | Lai |
| 2018/0250494 A1* | 9/2018 | Hanbury ........... A61B 5/6803 |
| 2019/0029878 A1 | 1/2019 | Linder et al. |
| 2019/0053948 A1 | 2/2019 | Schempp |
| 2019/0133815 A1* | 5/2019 | Nofzinger ........ A61F 7/007 |
| 2020/0170534 A1 | 6/2020 | Flaeschner et al. |
| 2020/0219615 A1 | 7/2020 | Rabin et al. |
| 2020/0306493 A1 | 10/2020 | Lee |
| 2020/0352821 A1 | 11/2020 | Wersland et al. |
| 2021/0008331 A1* | 1/2021 | Jin ............... H04R 1/1075 |
| 2021/0022955 A1 | 1/2021 | Wersland et al. |
| 2021/0128399 A1 | 5/2021 | Wersland et al. |
| 2021/0220210 A1 | 7/2021 | Berdahl et al. |
| 2021/0244611 A1 | 8/2021 | Wersland et al. |
| 2021/0259557 A1 | 8/2021 | Frank et al. |
| 2021/0286180 A1 | 9/2021 | Samec et al. |
| 2021/0330539 A1 | 10/2021 | Faussett |
| 2021/0401663 A1 | 12/2021 | Wersland et al. |
| 2022/0105359 A1 | 4/2022 | Rappaport |
| 2022/0241137 A1 | 8/2022 | Solana et al. |
| 2022/0257962 A1 | 8/2022 | Mogen et al. |
| 2023/0001131 A1 | 1/2023 | English et al. |
| 2023/0001191 A1 | 1/2023 | Schwarz et al. |

(56) References Cited

U.S. PATENT DOCUMENTS

| | | |
|---|---|---|
| 2023/0347102 A1 | 11/2023 | Nazarian et al. |
| 2023/0398324 A1 | 12/2023 | McVey et al. |
| 2024/0033466 A1 | 2/2024 | Nazarian et al. |

FOREIGN PATENT DOCUMENTS

| | | |
|---|---|---|
| CN | 201239336 Y | 5/2009 |
| CN | 301664182 S | 9/2011 |
| CN | 202637439 U | 1/2013 |
| CN | 103550029 A | 2/2014 |
| CN | 303250924 S | 6/2015 |
| CN | 303250929 S | 6/2015 |
| CN | 303793818 | 1/2016 |
| CN | 303798351 | 8/2016 |
| CN | 303826703 | 8/2016 |
| CN | 304016902 | 1/2017 |
| CN | 106511045 A | 3/2017 |
| CN | 106859949 A | 6/2017 |
| CN | 304337489 | 10/2017 |
| CN | 304402475 | 12/2017 |
| CN | 304461942 | 1/2018 |
| CN | 304561844 S | 3/2018 |
| CN | 304795155 | 8/2018 |
| CN | 207855923 U | 9/2018 |
| CN | 304875170 | 11/2018 |
| CN | 108938359 A | 12/2018 |
| CN | 304934022 | 12/2018 |
| CN | 304982787 | 1/2019 |
| CN | 109528473 A | 3/2019 |
| CN | 305250747 | 7/2019 |
| CN | 305275902 | 7/2019 |
| CN | 305302847 | 8/2019 |
| CN | 305318901 | 8/2019 |
| CN | 305327420 | 8/2019 |
| CN | 209347585 U | 9/2019 |
| CN | 305349253 | 9/2019 |
| CN | 305501003 | 12/2019 |
| CN | 305555921 | 1/2020 |
| CN | 305611712 | 2/2020 |
| CN | 210228475 U | 4/2020 |
| CN | 305726159 | 4/2020 |
| CN | 305738333 | 4/2020 |
| CN | 305775702 | 5/2020 |
| CN | 305852653 | 6/2020 |
| CN | 305872601 | 6/2020 |
| CN | 211067931 U | 7/2020 |
| CN | 305982060 | 8/2020 |
| CN | 305989858 | 8/2020 |
| CN | 306004590 | 8/2020 |
| CN | 306383446 | 9/2020 |
| CN | 306119091 | 10/2020 |
| CN | 306130382 | 10/2020 |
| CN | 306142072 | 10/2020 |
| CN | 306184674 | 11/2020 |
| CN | 306197232 | 11/2020 |
| CN | 306242891 | 12/2020 |
| CN | 306339053 | 2/2021 |
| CN | 306339102 | 2/2021 |
| CN | 306423578 | 3/2021 |
| CN | 306532932 | 5/2021 |
| CN | 306554191 | 5/2021 |
| CN | 213311563 U | 6/2021 |
| CN | 306623311 | 6/2021 |
| CN | 306682839 | 7/2021 |
| CN | 306724806 | 7/2021 |
| CN | 306754485 | 8/2021 |
| CN | 306778555 | 8/2021 |
| CN | 306798663 | 8/2021 |
| CN | 113679585 A | 11/2021 |
| CN | 306922350 | 11/2021 |
| CN | 214971144 U | 12/2021 |
| CN | 307035688 | 12/2021 |
| CN | 113952201 A | 1/2022 |
| CN | 215425988 U | 1/2022 |
| CN | 215606829 U | 1/2022 |
| CN | 307073094 | 1/2022 |
| CN | 215739868 U | 2/2022 |
| CN | 215839897 U | 2/2022 |
| CN | 307138150 | 3/2022 |
| CN | 307160397 | 3/2022 |
| CN | 216258666 U | 4/2022 |
| EM | EU000131743-0001 | 5/2004 |
| EM | EU000745187-0001 | 7/2007 |
| EM | EU001620709-0003 | 10/2009 |
| EM | EU001250096-0001 | 12/2010 |
| EM | EU002278416-0003 | 7/2013 |
| EM | EU003734482-0001 | 2/2017 |
| EM | EU006062022-0002 | 1/2019 |
| EM | EU007837737-0005 | 4/2020 |
| EM | EU007837737-0007 | 4/2020 |
| EM | EU007837737-0014 | 4/2020 |
| EM | EU008150635-0004 | 9/2020 |
| GB | 3024419 | 5/2006 |
| GB | 90005087670001 | 6/2006 |
| GB | 90007451870001 | 7/2007 |
| GB | 80767100001000 | 8/2011 |
| GB | 90037344820001 | 2/2017 |
| GB | 90058325810001 | 12/2018 |
| GB | 90060620220002 | 1/2019 |
| GB | 90078377370005 | 4/2020 |
| GB | 90078377370007 | 4/2020 |
| GB | 90078377370014 | 4/2020 |
| JP | S5428491 A | 3/1979 |
| JP | H0447440 U | 4/1992 |
| JP | 2000189525 A | 7/2000 |
| JP | 2011502369 A | 1/2011 |
| JP | 5129032 B2 | 1/2013 |
| JP | 2014511240 A | 5/2014 |
| KR | 300619292 | 11/2011 |
| KR | 101162978 B1 | 7/2012 |
| KR | 20170108550 A | 9/2017 |
| KR | 300925482 | 10/2017 |
| RU | 00118501 | 1/2020 |
| SG | 181413 A1 | 7/2012 |
| TW | I359657 B | 3/2012 |
| WO | WO-D07671-0001 | 9/2011 |
| WO | WO-2012074483 A1 | 6/2012 |
| WO | WO-2018013835 A4 | 3/2018 |
| WO | WO-2020149532 A2 | 7/2020 |
| WO | WO-D207075-001 | 9/2020 |
| WO | WO-D207075-002 | 9/2020 |
| WO | WO-2020219350 A1 | 10/2020 |
| WO | WO-2022056340 A1 | 3/2022 |
| WO | 2023172676 A2 | 9/2023 |

OTHER PUBLICATIONS

Amazon: "Bomoco Eye Massager with Heat and Vibration, AI Intellignet Voice Control Relxation Gifts for Women Men Rechargeable Intelligent Eye Mask," Posted at amazon.com, Posting date Apr. 27, 2022, [online], 9 Pages, [Site visited on Dec. 11, 2022], Retrieved from URL: https://www.amazon.com/dp/B09YY9B3W4/.

Amazon: "Breo iSee4 Eye Massager with Heat, Electric Massager for Dry Eye, Eye Strain, Eye Fatigue Relief & Better Sleep," Posted at Amazon.com, Posting date Jul. 7, 2020, [online], 10 Pages, [Site visited Dec. 11, 2022] Retrieved from URL: https://www.amazon.com/dp/B08CGS7C16/.

Amazon: "Cfeneyol Eye Massager, Smart Eye Mask With Heating Pads, Warm Compress for Dry Eyes, Weighted Sleep Mask With Vibration for Eye Tension Relief, Christmas Gifts for Men," posted at amazon.com, Posting date Nov. 3, 2021, [online], 9 Pages, [Site visited on Dec. 11, 2022], Retrieved from URL: https://www.amazon.com/dp/B09KX3J2KP.

Amazon: "Eye Massager with Airbag Kneading, Constant Temperature Hot Compress, Multi-Frequency Vibration and Bluetooth Music (L, White)," TLINNA, First available Nov. 12, 2019, 10 Pages, Retrieved from URL: https://www.amazon.com/Massager-Temperature-Multi-Frequency-Vibration-Bluetooth/dp/B09PR7C6NC/ref=dp_coos_1?pd_rd_i=B09PR7C6NC&psc=1.

Amazon: "Renpho Eye Massager with Heat, Compression, Remote Control, Bluetooth, Eye & Temple Massage Mask for Relax Eye

(56) References Cited

OTHER PUBLICATIONS

Strain, Reduce Dark Circles, Dry Eyes, Improve Sleep, Christmas Gifts Delay Eye Aging," Posted at amazon.com, Posting date Jul. 16, 2020, [online], 15 Pages, [Site visited Dec. 11, 2022], Retrieved from URL: https://www.amazon.com/RENPHO-Updated-Compression-Bluetooth-Rechargeable/dp/B088BJ8B1G.

Anthony Katz, "The Raptor: Helps Patients and Saves Your Most Valuable Tool . . . Your Hands," DC Aligned:MeyerDC, Dec. 9, 2015, available at: http://news.meyerdc.com/community/vendor-spotlight/the-raptor-helps-patients-saves-your-most-valuable-tool-your-hands/ (last visited Feb. 15, 2023); 5 pages.

Deanlong: "How Does an Eye Massager Help in Eye Strain & Eye Fatigue Relief?," Jun. 14, 2022, 17 Pages, Downloaded Nov. 22, 2022, Retrieved from URL: https://www.deanlong.io/blog/how-does-an-eye-massager-help-in-eye-strain-eye-fatigue-relief.

Defendant's Initial Invalidity Contentions, *Therabody, Inc.* v. *Tzumi Electronics LLC et al.*, Case No. SDNY-1-21-cv-07803 (PGG)(RWL), dated Aug. 17, 2022; 16 pages.

Description of Therabody GI Device, available at: https://www.therabody.com/us/en-us/faq/thearagun-devices/faq-devices-1.html?fdid=faq&csortb1=sortOrder&csortd1=1 (last visited Feb. 15, 2023).

Holly Riddle, "Theragun vs. Hyperice vs, Hydragun: Massage Gun Showdown [Buyer's Guide]," ChatterSource: Health & Wellness, Mar. 9, 2021, available at: https://www.chattersource.com/article/massage-gun/ (last visited Feb. 17, 2023); 14 pages.

International Search Report and Written Opinion for International Application No. PCT/US2023/019392 mailed Aug. 3, 2023, 15 pages.

Madaus S., "The Therabody SmartGoggles, High-Tech Device Brings the Theragun Treatment to your Eyes," Posted at self.com, Posting date Sep. 20, 2022, [online], 12 Pages, [site visited Nov. 12, 2022], Retrieved from URL: https://www.self.com/story/therabody-smartgoggles.

Mazzagers: "An Eye Massage Greatly Reduces Stress, Anxiety and Promotes Good Mental Health," Jan. 17, 2020, 06 Pages, Nov. 22, 2022, Retrieved from URL: https://mazzagers.com/eye-massager-stress-relief/.

Rhmip: "Eye Massager With Heat, Bluetooth Music Rechargeable Eye Heat Massager, Relax and Reduce Eye Starin Dark Circles Eye Bags Dry Eye, Ldeal Gift for Both Men and Women (White)," Posted at Amazon.com, Posting date Oct. 23, 2021, [online], 10 Pages, [Site visited Dec. 11, 2022], Retrieved from URL: https://www.amazon.com/dp/B09K4LK8ZQ/.

SereneLife: "SereneLife SLEYMSG40 Smart Eye Massager with Heat and Presssure Point Therapy," posted atwalmart.com, posting date Nov. 30, 2021, [online], 9 Pages, [site visited Dec. 11, 2022], Retrieved from URL: https://www.walmart.com/ip/SereneLife-SLEYMSG40-Smart-Eye-Massager-with-Heat-Pressure-Point-Therapy/390691257.

Venkatesan S., Dr., MD., "Oculo Cardiac Reflex: An Unique Neural Link Between the Eyes and Heart," Feb. 3, 2015, 7 Pages, Nov. 22, 2022, Retrieved from URL: https://drsvenkatesan.com/tag/eye-ball-massage/.

Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.

Visual Description of Hyper Ice, Inc. Raptor Device, "Raptor Solutions 1.3 Prone," available at: https://www.youtube.com/watch?v=6i1tRqdwPU8&t=156s (last visited Feb. 15, 2023); 1 page.

* cited by examiner

Example Heart Rate Control – Target 50 BPM

| Dynamic Period | User Heart Rate | Percentage | Pulse Rate Calculation | Pulse rate |
|---|---|---|---|---|
| 1 | 88 | 100% | 100% x 88 = 88 | 60 |
| 2 | 82 | 97% | 97% x 82 = 80 | 60 |
| 3 | 75 | 94% | 94% x 75 = 71 | 60 |
| ... | ... | ... | ... | ... |
| 13 | 60 | 64% | 64% x 60 = 38 | 38 |
| 14 | 58 | 61% | 61% x 58 = 35 | 35 |
| 15 | 56 | 58% | 58% x 56 = 32 | 32 |

FIG. 23

Example Heart Rate Control – Target 45 BPM

| Dynamic Period | User Heart Rate | Percentage | Pulse Rate Calculation | Pulse rate |
|---|---|---|---|---|
| 1 | 54 | 100% | 100% x 54 = 54 | 54 |
| 2 | 51 | 97% | 97% x 51 = 80 | 49 |
| 3 | 49 | 94% | 94% x 49 = 71 | 46 |
| ... | ... | ... | ... | ... |
| 13 | 45 | 64% | 64% x 45 = 29 | 45 |
| 14 | 45 | 61% | 61% x 45 = 27 | 45 |
| 15 | 45 | 58% | 58% x 45 = 26 | 45 |

FIG. 24

Example Heart Rate Control – Target 50 BPM

| Dynamic Period | User Heart Rate | Percentage | Pulse Rate Calculation | Pulse rate |
|---|---|---|---|---|
| 1 | 40 | 100% | 100% x 40 = 40 | 40 |
| 2 | 41 | 103% | 103% x 41 = 42 | 42 |
| 3 | 43 | 106% | 106% x 43 = 46 | 46 |
| ... | ... | ... | ... | ... |
| 8 | 48 | 121% | 121% x 48 = 58 | 62 |
| 9 | 50 | 124% | 124% x 50 = 62 | 50 |
| 10 | 50 | 127% | 127% x 50 = 64 | 50 |

FIG. 25

Example Relaxation Preset Function

| Function | Relaxation (Default) | Function modifier |
|---|---|---|
| Heat | Low | 1. Medium<br>2. High<br>3. Off<br>4. Low (default) |
| Vibration | Heart rate control<br>(See FIGS. 23 and 24) | 1. Off<br>2. Resume heart rate control |
| Airbag Inflation | 1. Inflate temple bladders (104, 108) – 5 seconds<br>2. Hold inflation of temple bladders (104, 108) – 5 seconds<br>3. Deflate temple bladders (104, 108) – 5 seconds<br>4. Inflate center bladders (128, 130) – 5 seconds<br>5. Hold inflation of center bladders (128, 130) – 5 seconds<br>6. Deflate center bladders (128, 130) – 5 seconds<br>7. Repeat. | |

FIG. 26

Example Focus Preset Function

| Function | Focus (Default) | Function modifier |
|---|---|---|
| Heat | Medium | 1. High<br>2. Off<br>3. Low<br>4. Medium (default) |
| Vibration | Wave | 1. Low<br>2. High<br>3. Off<br>4. Wave (default) |
| Airbag Inflation | 1. Inflate center bladders (128, 130) – 4 seconds<br>2. Hold inflation of center bladders (128, 130) – 4 seconds<br>3. Deflate center bladders (128, 130) – 4 seconds<br>4. Inflate eye bladders (112, 114, 116, 118) – 4 seconds<br>5. Hold inflation of eye bladders (112, 114, 116, 118) – 4 seconds<br>6. Deflate eye bladders (112, 114, 116, 118) – 4 seconds<br>7. Inflate temple bladders (104, 108) – 4 seconds<br>8. Hold inflation of temple bladders (104, 108) – 4 seconds<br>9. Deflate temple bladders (104, 108) – 4 seconds<br>10. Repeat. | |

FIG. 27

Example Sleep Preset Function

| Function | Sleep (Default) | Function modifier |
|---|---|---|
| Heat | Off | 1. Low<br>2. Medium<br>3. High<br>4. Off (default) |
| Vibration | Low | 1. High<br>2. Wave<br>3. Off<br>4. Low (default) |
| Airbag Inflation | 1. Inflate temple bladders (104, 108) – 6 seconds<br>2. Hold inflation of temple bladders (104, 108) – 6 seconds<br>3. Deflate temple bladders (104, 108) – 6 seconds<br>4. Repeat. | |

FIG. 28

FACIAL WEARABLE DEVICE AND METHODS FOR PROVIDING EXTERNAL STIMULI USING THE SAME

CROSS REFERENCE TO RELATED APPLICATIONS

This application in a divisional of U.S. patent application Ser. No. 17/933,419, filed Sep. 19, 2022, which is a continuation of U.S. Provisional Patent Application No. 63/335,540, filed Apr. 27, 2022. Each of these prior-filed applications are incorporated herein by reference in their entirety.

BACKGROUND

Technical Field

Aspects of the present disclosure relate to facial wearable devices and methods for providing external stimuli to users via the facial wearable devices, alone or in combination with accessory devices, where the external stimuli may include audio and/or physical stimuli.

Background

The mind and the body are connected. A person's physical health affects their mind, just as the state of their mind influences their body. Taking steps to improve their physical health can help a person's mind, and vice versa.

Engaging in intentional mind-body practices to help change or regulate a person's mind-body state can be important for optimal performance, focus, relaxation, sleep, and well-being. A number of mind-body practices, such as yoga and meditation, are well known. Engagement in these sorts of mind-body practices can provide various health benefits, such as reducing blood pressure, heart rate, respiratory rate, stress, anxiety, and pain intensity. Mind-body practices can also be used to improve immune response, neural connectivity, and arousal levels.

Successful engagement in mind-body practices such as yoga and meditation often requires training by and practice with an instructor, and learning and following formal techniques. There can be a steep learning curve associated with these practices and mastering their techniques. And these mind-body practices are often conducted in the absence of external stimuli, or with only limited external stimuli such as music, so that the person engaged in the activity can focus on their practice and techniques.

Various therapeutic treatments or practices can be used to engage different parts of the body, including common areas such as large muscle groups or joints. But a user's head and face, including the eyes and surrounding tissue, are also an important area of potential treatment. As people age and experience increasing amounts of screen time, therapeutic devices for facial treatments may provide benefits. Facial treatments, including eye area facial massage, may be used to alleviate eyestrain, eye puffiness, dry eyes, headaches, and to stimulate ocular blood flow, as well as to improve sleep quality.

However, even when facial treatments are used, if some form of external stimuli is included, the external stimuli is often generically designed and is generically presented with a one-size fits all approach in a simple device or system. Moreover, existing facial treatment devices and methods do not communicate with other computing devices such as mobile phones, and do not employ sensors or enable biofeedback based on heart rate, respiration rate, or other metrics.

SUMMARY

Accordingly, there is a need for new and improved facial wearable devices and methods for providing external stimuli to users via the facial wearable devices, alone or in combination with accessory devices. This includes but is not limited to systems and methods for providing air chamber inflation stimulation, vibration stimulation, and targeted heat stimulation to the facial area of a user through external stimuli to address one or more of the above issues.

A facial wearable device for providing external stimuli to a user may include a foldable frame, a flexible layer, an airbag layer, a plurality of heating pads, a plurality of vibrating motors, and a sensor. The flexible layer may couple to a proximal side of the foldable frame and be configured to couple to a facial area of the user. The airbag layer may be disposed between the foldable frame and the flexible layer, and couple with the foldable frame. The airbag layer may include a plurality of inflatable bladders configured to provide pressure to the facial area of the user. The plurality of heating pads may couple to the flexible layer and be configured to provide heat to the facial area of the user. The plurality of vibrating motors may couple to the flexible layer and be configured to provide vibration to the facial area of the user. The sensor may couple to the flexible layer and be configured to detect biometric data of the user. In some embodiments, at least one of the plurality of inflatable bladders, the plurality of heating pads, and the plurality of vibrating motors may be controlled based on the biometric data.

In some embodiments, the facial wearable device may further include a communication unit configured to communicate with a separate device that is capable of providing feedback based on the biometric data to the user. In some embodiments, the foldable frame may include a left frame pivotably coupled to a right frame with a hinge. The hinge may be configured to pivot around a first axis. In some embodiments, the facial wearable device may include a top edge, a bottom edge, and a nose bridge. The nose bridge may include an apex running across the bottom edge. In some embodiments, the facial wearable device may include a left side and a right side divided by the first axis. In some embodiments, a second axis may run across a width of the device perpendicular to the first axis. In some embodiments, the second axis may be located at a height halfway between the top edge of the device, where the first axis intersects the top edge of the device, and between the bottom edge at the apex of the nose bridge of the device, where the first axis intersects the apex. In some embodiments, the facial wearable device may include a upper side and a lower side divided by the second axis. In some embodiments, the device may include top-left, top-right, bottom-left, and bottom-right portions divided by the first axis and the second axis.

In some embodiments, at least one bladder of the plurality of inflatable bladders may be disposed in each of the top-left, top-right, bottom-left, and bottom-right portions. In some embodiments, at least one vibrating motor of the plurality of vibration motors may be disposed in each of the top-left, top-right, bottom-left, and bottom-right portions. In some embodiments, the plurality of vibration motors may be configured to operate independently in each of the upper and lower sides. In some embodiments, a first heating pad of the plurality of heating pads may be disposed in the bottom-left portion, and a second heating pad of the plurality of heating pads may be disposed in the bottom-right portion.

In some embodiments, at least two bladders of the plurality of inflatable bladders and at least two vibrating members of the plurality of vibrating motors may be disposed in each of the top-left and top-right portions. In some embodiments, at least one bladder of the plurality of inflatable bladders, at least one vibrating member of the plurality of vibrating motors, and at least one heating pad of the plurality of heating pads may be disposed in each of the lower bottom-left and bottom-right portions.

According to another aspect of the present disclosure, a method of providing external stimuli to a user with a facial wearable device may include the steps of: coupling the facial wearable device to the user's facial area; selecting an operational mode for the device, where the operational mode may include a first external stimuli and a second external stimuli; activating a first external stimuli; and activating a second external stimuli. In some embodiments, the device may include a plurality of inflatable bladders, a plurality of heating pads, a plurality of vibrating motors, and a sensor configured to detect biometric data of the user. In some embodiments, the second external stimuli may be different from the first external stimuli but from the same type of actuator. In some embodiments, the first external stimuli may include actuation of one type of actuator including one of the plurality of inflatable bladders, the plurality of heating pads, and the plurality vibrating motors. In some embodiments, the second external stimuli may include actuation of a different one of the plurality of inflatable bladders, the plurality of heating pads, and the plurality vibrating motors.

In some embodiments, the facial wearable device may further include a top edge, a bottom edge, and a nose bridge having an apex running across the bottom edge. In some embodiments, the facial wearable device may further include a left side and a right side divided by a first axis. In some embodiments, a second axis may run across a width of the device perpendicular to the first axis. The second axis may be located at a height halfway between the top edge of the device, where the first axis intersects the top edge of the device, and between the bottom edge at the apex of the nose bridge of the device, where the first axis intersects the apex. In some embodiments, the facial wearable device may further include a upper side and a lower side divided by the second axis. The facial wearable device may include top-left, top-right, bottom-left, and bottom-right portions divided by the first axis and the second axis.

In some embodiments, the step of activating the first external stimuli may include inflating a first bladder of the plurality of inflatable bladders in a least one of the top-left, top-right, bottom-left, and bottom-right portions. In some embodiments, the step of activating the second stimuli may include inflating a second bladder of the plurality of inflatable bladders in a least one of the top-left, top-right, bottom-left, and bottom-right portions.

In some embodiments, the step of activating the first external stimuli may include inflating at least one bladder of the plurality of inflatable bladders for a first predetermined amount of time, and deflating the at least one bladder of the plurality of inflatable bladders for a second predetermined amount of time. In some embodiments, the first predetermined amount of time is greater than the second predetermined amount of time.

In some embodiments, the step of activating the first external stimuli may include operating at least one vibrating member of the plurality of vibrating motors located in the upper side of the device. In some embodiments, the step of activating the second external stimuli may include operating at least one vibrating member of the plurality of vibrating motors disposed in the lower side of the device.

According to another aspect of the present disclosure, a method of providing external stimuli to a user with a facial wearable device may include the steps of: coupling the facial wearable device to the user's facial area; collecting heart rate data of the user with a heart rate sensor; pulsating a first vibrating member and a second vibrating member at a first device pulse rate for a first period of time; and pulsating the first vibrating member and the second vibrating member at a second device pulse rate for a second period of time after the first period of time. In some embodiments, the heart rate sensor may be configured to detect heart rate data of the user. In some embodiments, the first vibrating member may be disposed in a first portion of the device. In some embodiments, the second vibrating member may be disposed in a second portion of the device that differs from the first portion of the device. In some embodiments, the first device pulse rate and the second device pulse rate may be based on the heart rate data of the user.

In some embodiments, the first vibrating member may vibrate at a first intensity and the second vibrating member may vibrate at a second intensity different from the first intensity. In some embodiments, the first vibrating member and the second vibrating member may pulsate in a sequential rhythm similar to a human heart rhythm.

In some embodiments, the first and second device pulse rates may be between a range of about 60 pulses per minutes and 24 pulses per minutes. In some embodiments, the method may further include the step of operating the device in a relaxation mode. In the relaxation mode, the second device pulse rate may be less than the first device pulse rate. In some embodiments, the method may further include the step of operating the device in an energize mode. In the energize mode, the second device pulse rate may be higher than the first device pulse rate.

In some embodiments, the method may further include the step of communicating heart rate data to a separate user device to enable displaying the heart rate of the user over the first period of time and the second period of time on the separate user device. In some embodiments, the method may further include the step of the device entering an operational mode. In the operational mode the first device pulse rate may be equal to the lesser of the heart rate of the user or an upper limit pulse rate of the device. In some embodiments, in the operational mode, the second device pulse rate may be equal to the lesser of a first percentage of the heart rate of the user or the upper limit pulse rate of the device.

According to another aspect of the present disclosure, an eye massage wearable device may provide therapeutic treatments to and around a user's eyes. The wearable device may, for example, target pressure points around the face and eyes. In some embodiments, the eye massager may include both an arrangement of one or more air chambers and one or more vibration elements. The air chambers may be arranged within a layer element to provide additional comfort to the user, such that the vibration is dampened for sensitive areas of the face. The vibrating motors may be placed in therapeutically advantageous positions, such as adjacent to acupuncture pressure points around the eyes. The heating pads may be placed in therapeutically advantageous positions, such as below the eye sockets to provide relaxation. In some embodiments, vibrating motors may be placed in an adjustable headband of the eye massager.

Further features and advantages, as well as the structure and operation of various aspects, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art based on the teachings contained herein.

BRIEF DESCRIPTION OF THE DRAWINGS

The accompanying drawings, which are incorporated herein and form a part of the specification, illustrate embodiments of the present disclosure and, together with the description, further serve to explain the principles of the disclosure and to enable a person skilled in the pertinent art to make and use the disclosure.

FIG. 23 is a chart showing steps of a heart control protocol in accordance with a method of performing a therapy routine with a facial wearable device, according to an embodiment of the present disclosure.

FIG. 24 is a chart showing steps of a second heart control protocol in accordance with a method of performing a therapy routine with a facial wearable device, according to an embodiment of the present disclosure.

FIG. 25 is a chart showing steps of a third heart control protocol in accordance with a method of performing a therapy routine with a facial wearable device, according to an embodiment of the present disclosure.

FIG. 26 is a chart showing a relaxation mode for operating external stimuli of a facial wearable device in accordance with a method of performing a therapy routine with the facial wearable device, according to an embodiment of the present disclosure.

FIG. 27 is a chart showing a focus mode for operating external stimuli of a facial wearable device in accordance with a method of performing a therapy routine with the facial wearable device, according to an embodiment of the present disclosure.

FIG. 28 is a chart showing a sleep mode for operating external stimuli of a facial wearable device in accordance with a method of performing a therapy routine with the facial wearable device, according to an embodiment of the present disclosure.

Figure 1:
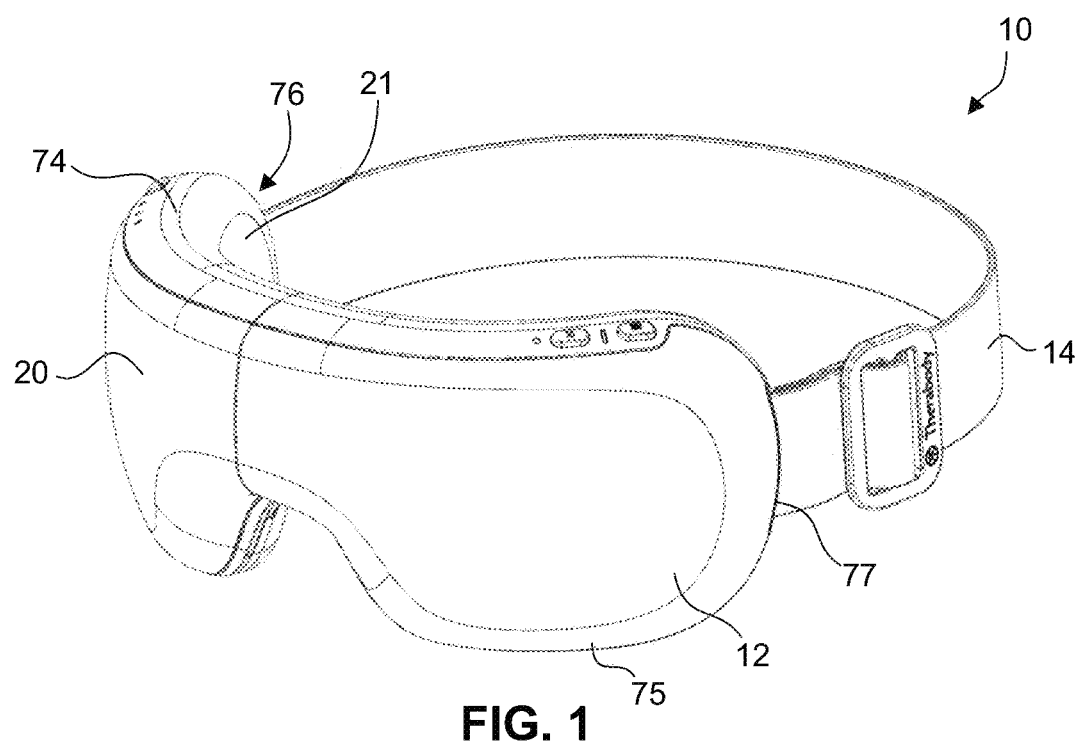
FIG. 1 illustrates a perspective view of a facial wearable device, according to an embodiment of the present disclosure.

Embodiments of the present disclosure will be described with reference to the accompanying drawings.

DETAILED DESCRIPTION

Provided herein are facial wearable devices and methods for providing external stimuli to users via the facial wearable devices, alone or in combination with accessory devices.

It will be appreciated that terms such as "front," "back," "proximal," "distal," "top," "bottom," "up," "down," "aft," "forward," "inboard," "outboard," "right," "left," and "below" used herein are merely for ease of description and refer to the orientation of the components as shown in the figures and relative to the user when the device is worn by the user. It should be understood that any orientation of the components described herein is within the scope of the present disclosure.

When used herein, the term "coupled to" or the like is intended to cover links or connections between components that are both direct or indirect (i.e., via intermediaries), unless the form of coupling is otherwise explicitly described as being only either direct or indirect.

Embodiments herein describe an innovative device that can provide a user with external stimuli, such as audio and/or physical stimuli, to enhance performance, focus, relaxation, sleep, and well-being. A facial wearable device 10 may be provided with a plurality of stimulation functions in the form of external stimuli. The external stimuli may include, for example, a plurality of inflatable airbag bladders, vibration motors, and/or heating pads that may target acupoints of a user's face. In some embodiments, one form of external stimuli, or combinations of one or more of the external stimuli, may be used to alter the mind-body state of the user or otherwise contribute to enhance performance, focus, relaxation, sleep, and well-being. The facial wearable device 10 may be a smart mask or goggles that may be implemented with an intelligent recommendation engine that considers user input, biofeedback from biosensors, and prior use effectiveness to curate a single-sense or multi-sensory experience for the user. Example intelligent recommendation engines are described in U.S. Patent App. Pub. No. 2021/0022955, which is incorporated herein by reference in its entirety.

The facial wearable device 10 may include an eye cover 12 and a headband 14 as shown, for example, in FIGS. 1 and 5-9. Eye cover 12 may be shaped to cover the eyes and surrounding facial areas of a user such that external stimuli in the eye cover, as described in more detail below, may provide massaging and therapeutic functions to acupoints of the user's face. Headband 14 may be coupled to the eye cover 12 and loop around the back of the head of the user to form a recess sized to accommodate the head of the user. In some embodiments, headband 14 may include adjustment means to adjust the length of headband 14 to accommodate different sized heads. In some embodiments, headband 14 may be made from elastic material and configured to stretch around the head of the user and provide an inward force to maintain a coupled relationship with the user's head. In some embodiments, vibration motors (not shown) may be coupled with the headband 14 at evenly spaced intervals or at locations to target portions of user's head. An illustrative example of an embodiment of the facial wearable device 10 arranged on the head of the user is shown in FIG. 2. In other embodiments, the facial wearable device 10 may not include a headband 14 and may be otherwise securable to the user's face.

Figure 2:
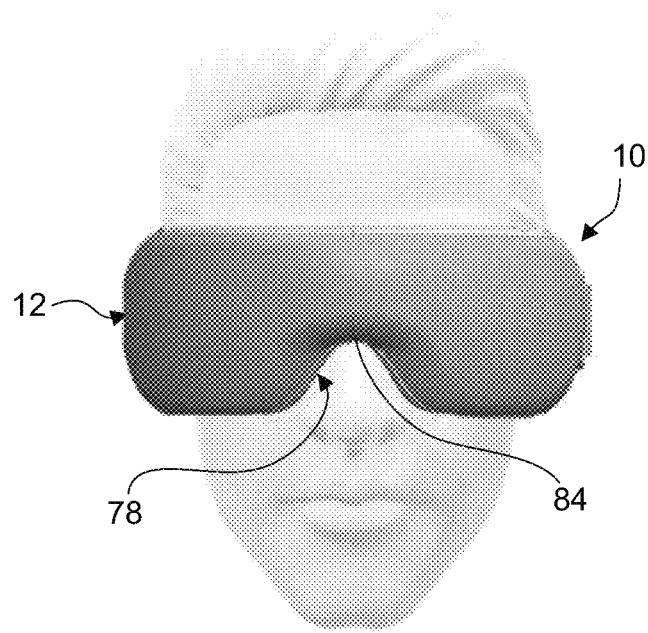
FIG. 2 illustrates an example of a user wearing a facial wearable device and positioning the wearable device to cover the eyes and surrounding facial area of the user, according to an embodiment of the present disclosure.
Figure 9:
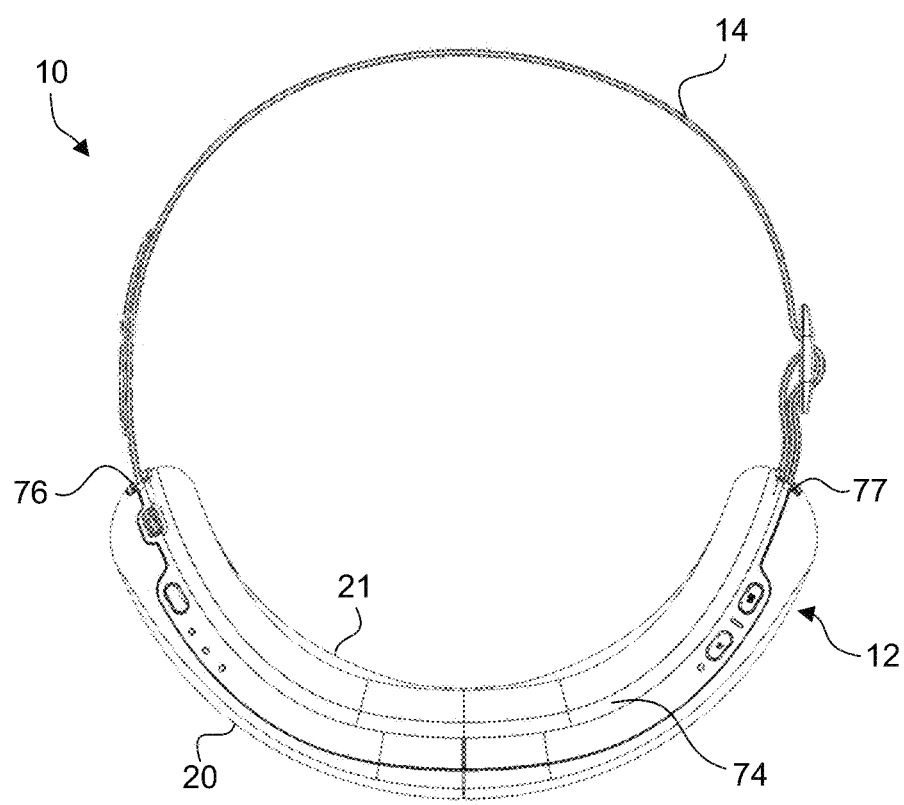
FIG. 9 illustrates a top view of a facial wearable device, according to an embodiment of the present disclosure.

Eye cover 12 may be shaped to accommodate the curvature of the user's head as shown, for example, in FIGS. 1 and 9. In the illustrative embodiments in FIGS. 1 and 9, eye cover 12 extends over the user's temples and extends forward around the front of the head of the user to cover the user's eyes and surrounding areas. Eye cover 12 includes a nose bridge 78 such that eye cover 12 can be arranged flush with the user's face, around the user's nose. Nose bridge 78 may contact the user's nose to provide support to eye cover 12 and avoid eye cover 12 slipping downward. Eye cover 12 may be configured to rest approximately on an apex 84 of nose bridge 78. Eye cover 12 may include top edge 74, bottom edge 75, right edge 76, and left edge 77 as shown, for example in FIGS. 1 and 5-9. Headband 14 may couple to eye cover 12 at the right and left edges 76, 77.

Figure 5:
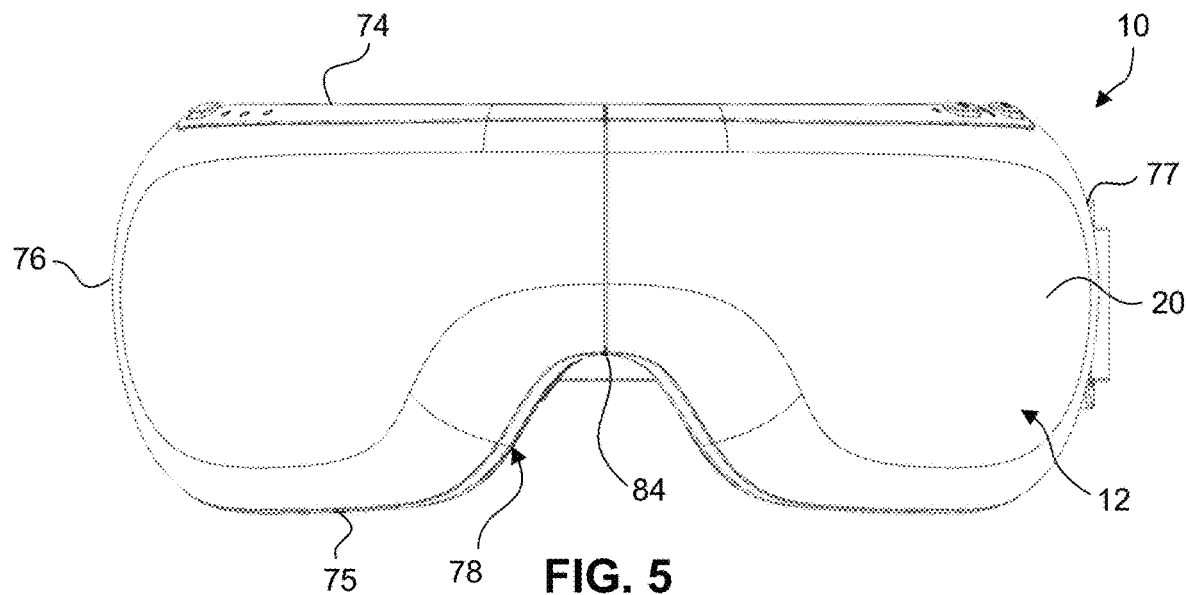
FIG. 5 illustrates a front view of a facial wearable device, according to an embodiment of the present disclosure.
Figure 6:
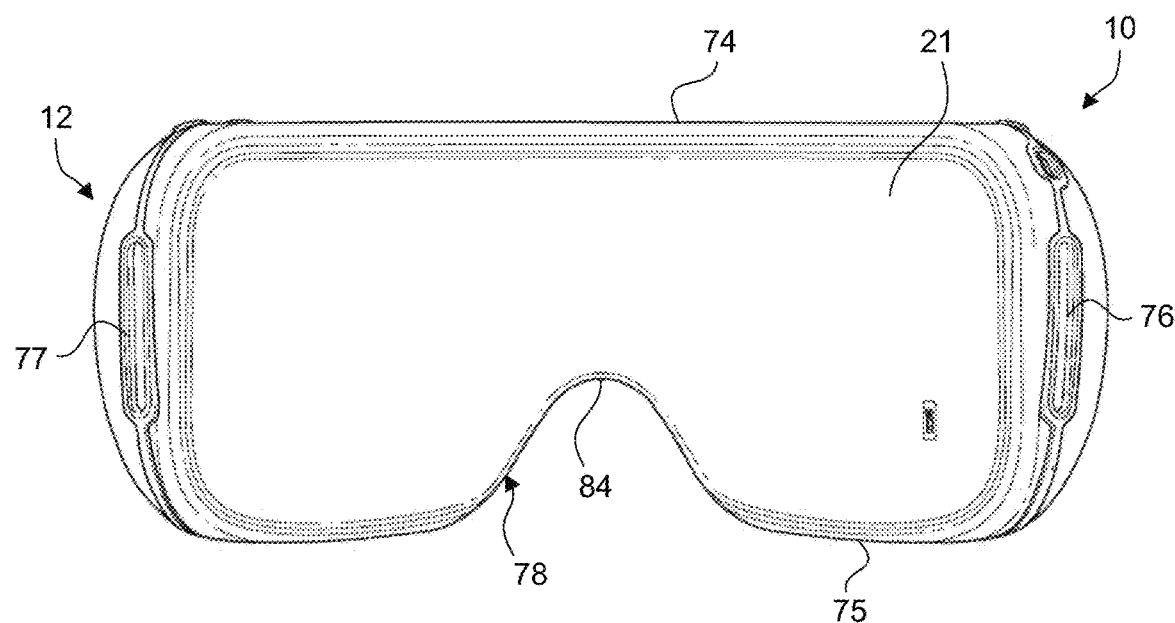
FIG. 6 illustrates a rear view of a facial wearable device with the headband removed, according to an embodiment of the present disclosure.
Figure 7:
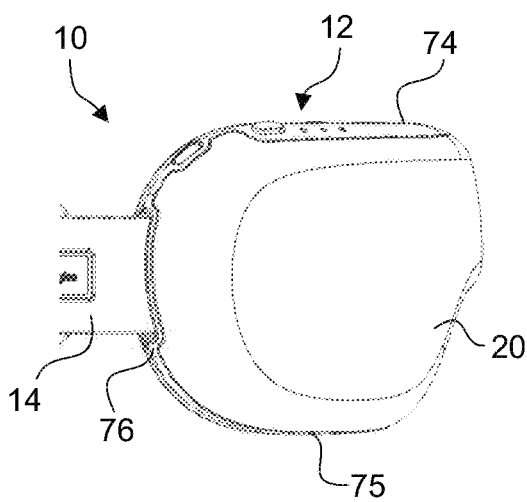
FIG. 7 illustrates a right side view of a facial wearable device, according to an embodiment of the present disclosure.
Figure 8:
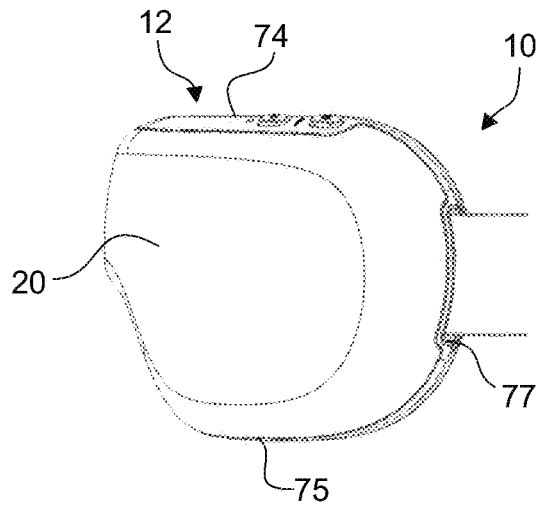
FIG. 8 illustrates a left side view of a facial wearable device, according to an embodiment of the present disclosure.

Eye cover 12 may further include a distal cover 20 and a proximal cover 21 as shown, for example in FIGS. 1, 5, and 6. Distal cover 20 and proximal cover 21 may form exterior surfaces of eye cover 12 and may protect the electronic components and external stimuli devices housed within the eye cover 12. Proximal cover 21 may couple with the user's face and may be made of a material to enhance comfort to the user when wearing the facial wearable device 10. Distal cover 20 may be arranged on the opposite side of eye cover 12 to the proximal cover 21, away from the user's face. In some embodiments, distal cover 20 may be made from the same material as the proximal cover 21. In some embodiments, distal cover 20 may be made from a hard material to provide protection to the electronic components and external stimuli devices housed therein. In some embodiments, distal cover 20 may include foam padding, or similar flexible material, to give a smooth outer surface appearance of the facial wearable device 10.

Figure 3:
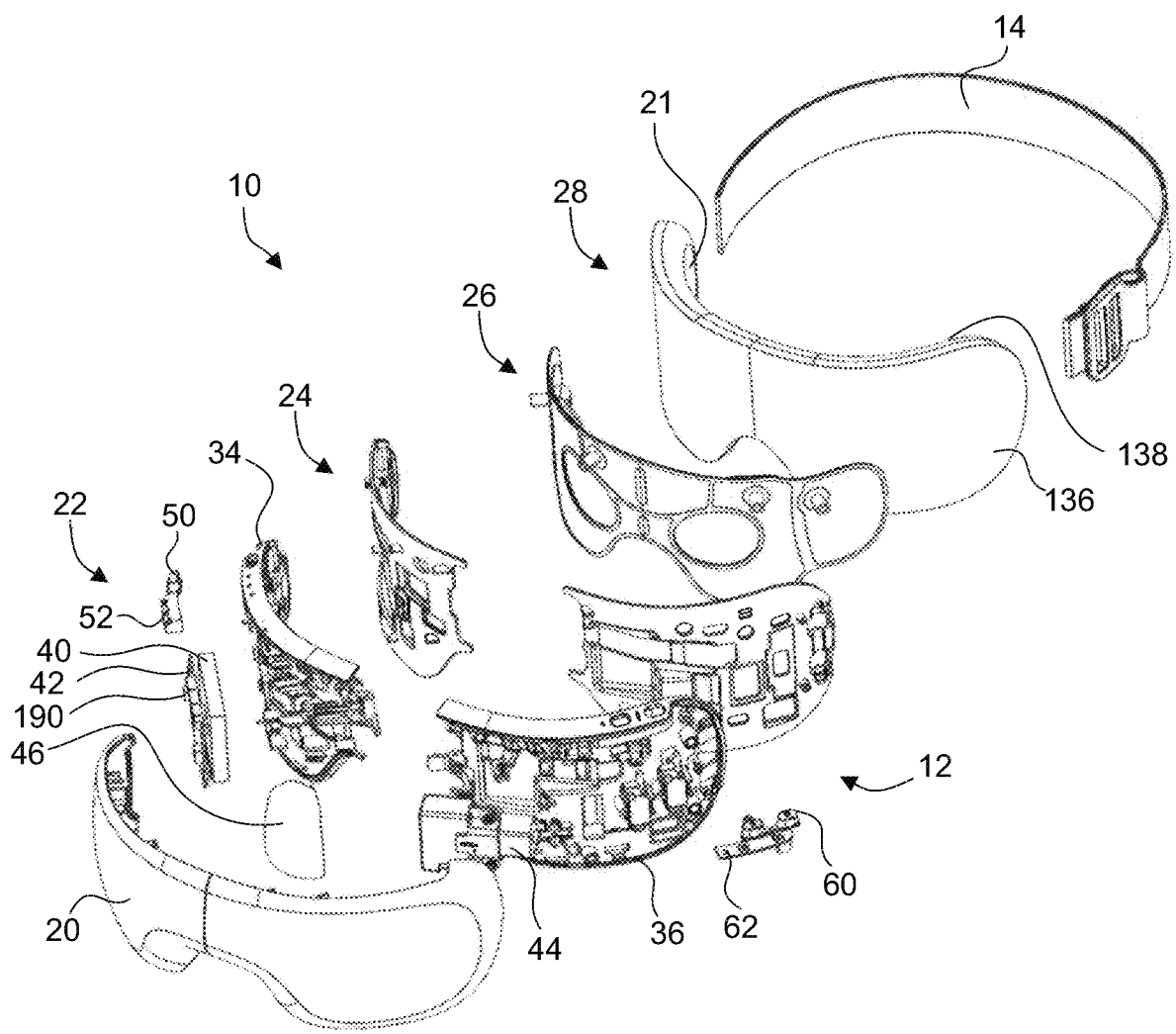
FIG. 3 illustrates an exploded front perspective view of a facial wearable device, according to an embodiment of the present disclosure.
Figure 4:
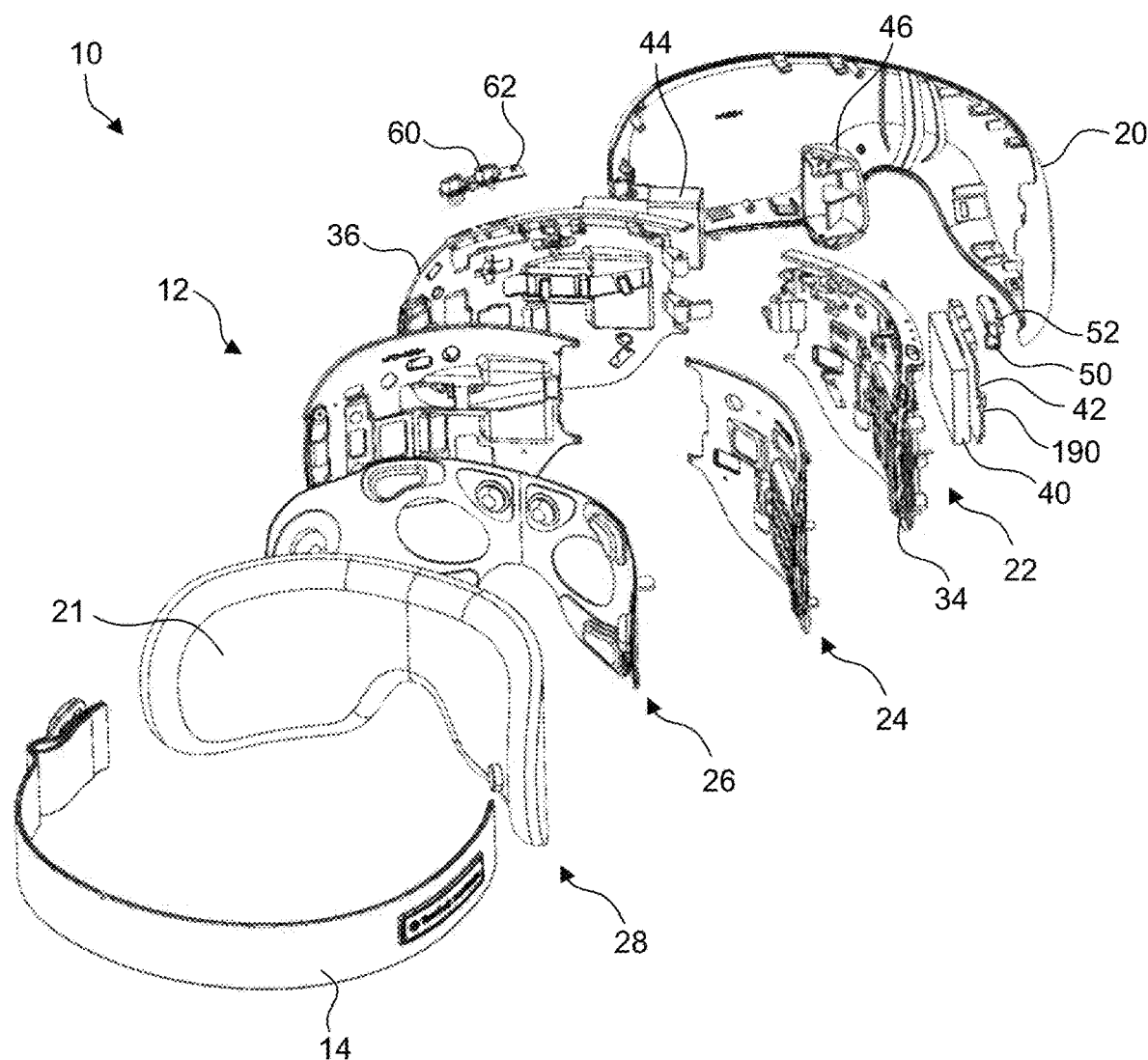
FIG. 4 illustrates an exploded rear perspective view of a facial wearable device, according to an embodiment of the present disclosure.
Figure 10:
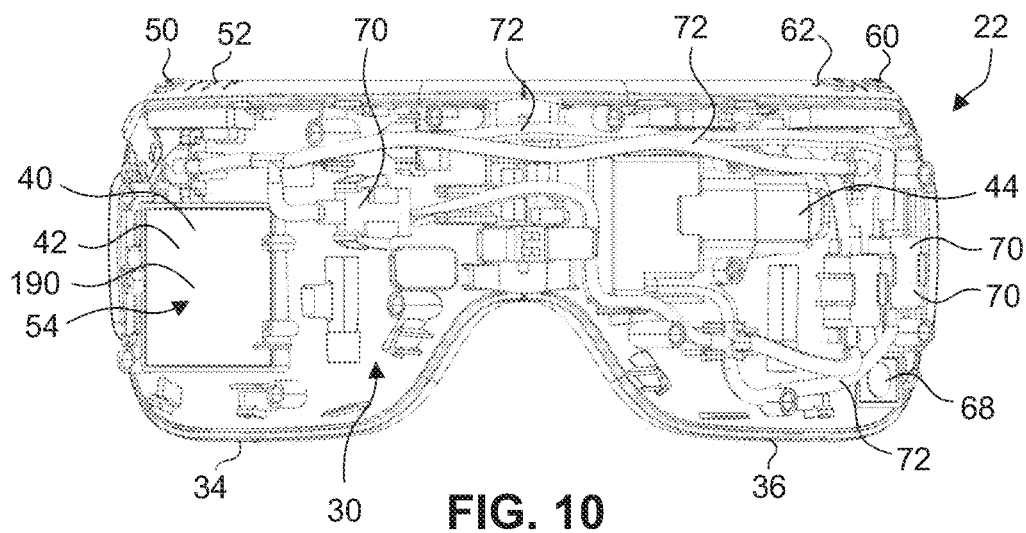
FIG. 10 illustrates a front view of a foldable frame of a facial wearable device, according to an embodiment of the present disclosure.
Figure 11:
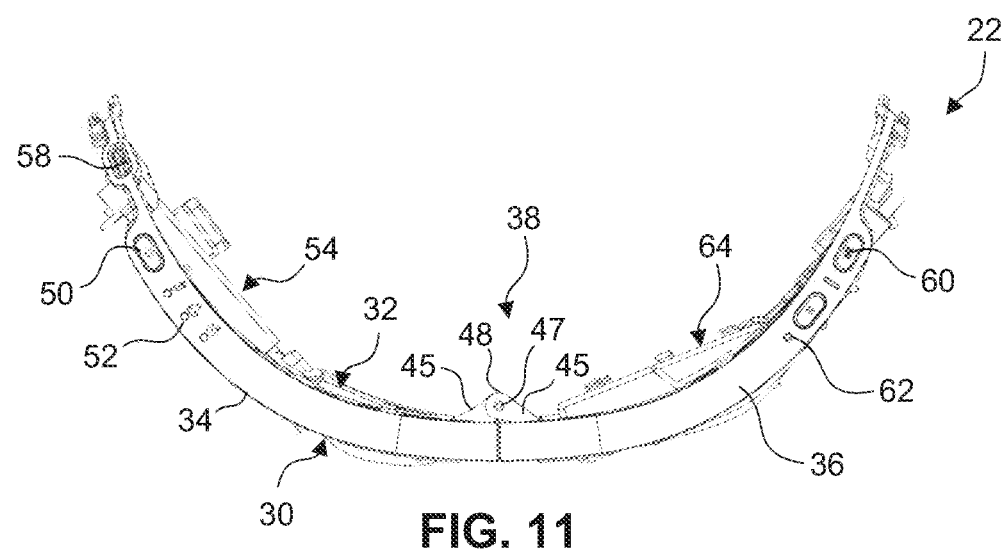
FIG. 11 illustrates a top view of a foldable frame of the facial wearable device, according to an embodiment of the present disclosure.
Figure 12:
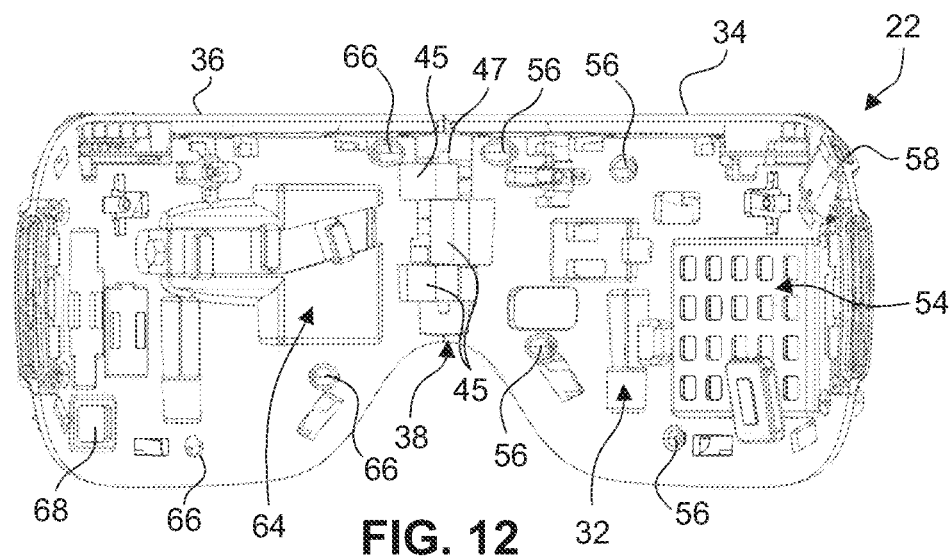
FIG. 12 illustrates a rear view of a foldable frame of the facial wearable device, according to an embodiment of the present disclosure.
Figure 13:
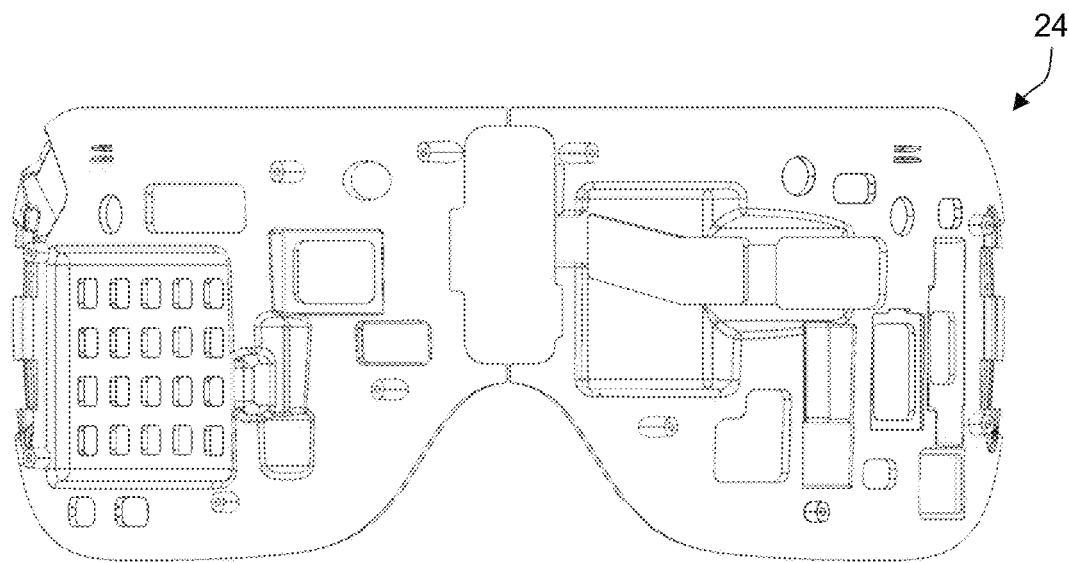
FIG. 13 illustrates a front view of a support layer of a facial wearable device, according to an embodiment of the present disclosure.
Figure 14:
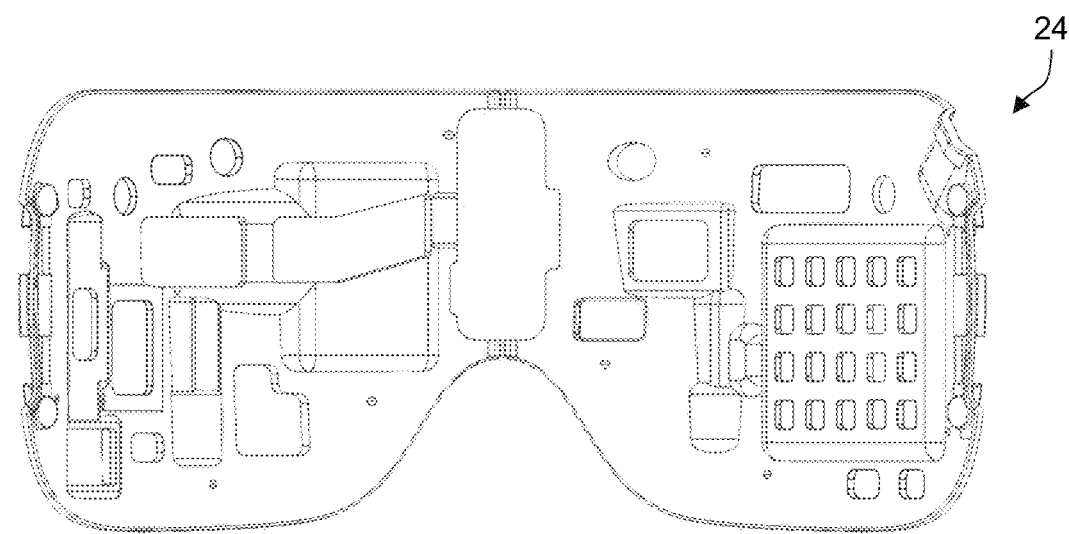
FIG. 14 illustrates a rear view of a support layer of a facial wearable device, according to an embodiment of the present disclosure.
Figure 17:
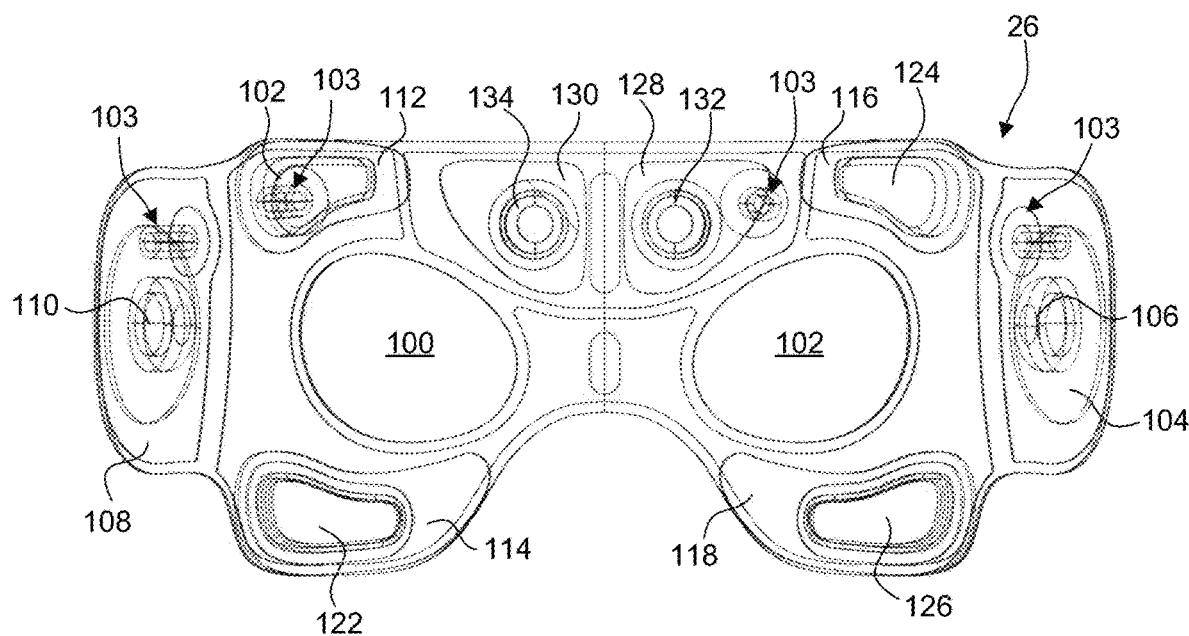
FIG. 17 illustrates a rear view of an airbag layer of a facial wearable device, according to an embodiment of the present disclosure.
Figure 18:
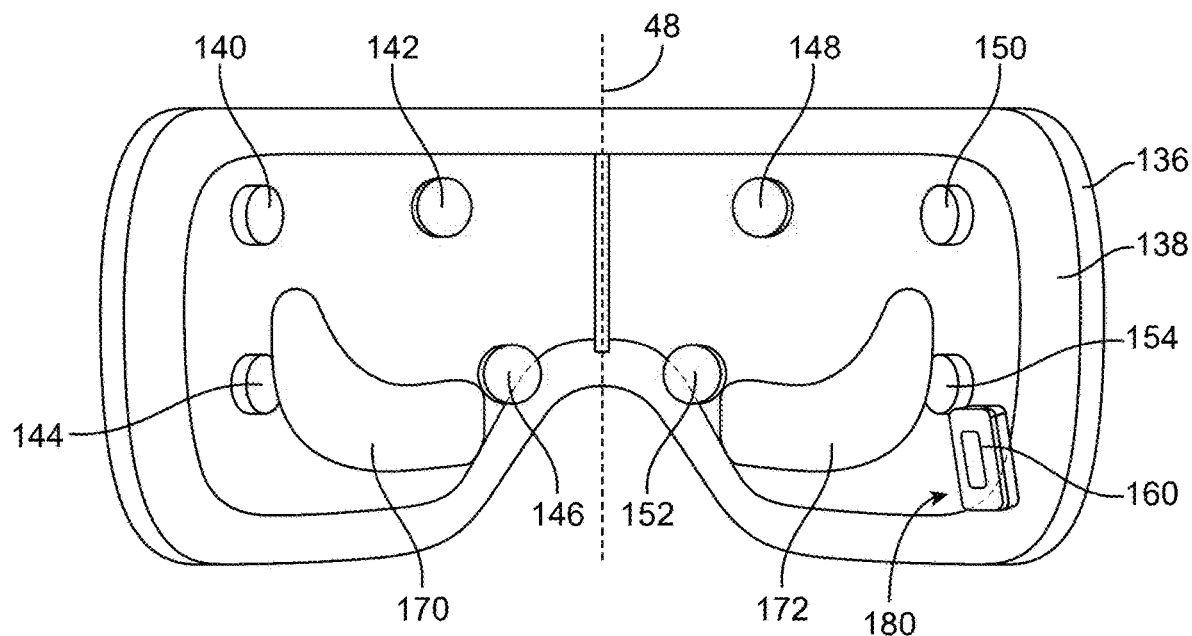
FIG. 18 illustrates a rear transparent view of a flexible layer of a facial wearable device showing a plurality of vibration motors, heating pads, and a sensor coupled with the flexible layer, according to an embodiment of the present disclosure.
Figure 19:
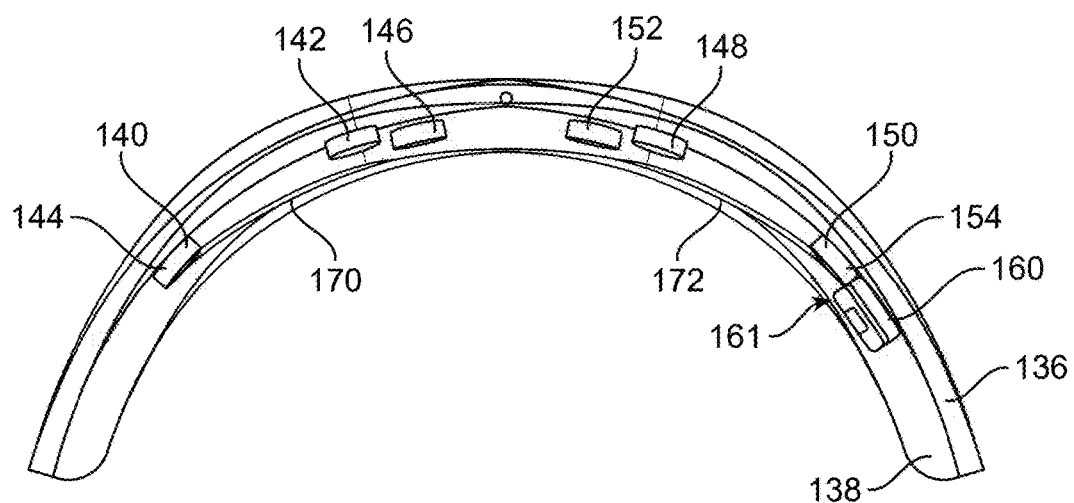
FIG. 19 illustrates a top transparent view of a flexible layer of a facial wearable device, according to an embodiment of the present disclosure.

Eye cover 12 may further include one or more of a plurality of layers 22, 24, 26, 28 and have a layered construction as shown, for example, in FIGS. 3 and 4. Each of the plurality of layers 22, 24, 26, 28 may provide structural support to couple the different electronic components or external stimuli devices to. In some embodiments, the layers may consist of a single, major structure, while in other embodiments, the layers may consist of two or more major sub-layer components, i.e. left and right side components of a layer. Eye cover 12 may include foldable frame 22, support layer 24, airbag layer 26, and flexible layers 28. Distal cover 20 may be coupled to a distal side 30 of the foldable frame 22. Illustrative embodiments of foldable frame 22 are shown in FIGS. 10-12. Support layer 24 may couple to a proximal side 32 of foldable frame 22 and may provide support to airbag layer 26. Illustrative embodiments of support layer 24 are shown in FIGS. 13 and 14. Airbag layer 26 may be located substantially between support layer 24 and proximal cover 21, in that the bulk of the airbag layer 26 may be located between support layer 24 and proximal cover 21, but that some portions of the airbag layer 26 may or may not extend beyond, over, or through support layer 24 and proximal cover 21. An illustrative embodiment of airbag layer 26 is shown in FIG. 17. Flexible foam layers 28 may be arranged over airbag layer 26 and may be covered by proximal cover 21, adjacent to the user's face. Illustrative embodiments of flexible layers 28, such as layers made of a foam, are shown in FIGS. 18 and 19. In some embodiments, a perimeter edge of flexible layers 28 clamps at an interface between foldable frame 22 and support layer 24 to couple flexible layers 28 to foldable frame 22. In some embodiments, flexible layers 28 may comprise one or more moldable or flexible materials with elasticity, such that the material(s) of the flexible layers 28 allow for movement of the airbag layers 26. In some embodiments, flexible layers 28 may be referred to herein as one or more flexible layers, soft material layers, foam layers, and/or cushion layers. In some embodiments, flexible layers 28 may be made of one or more materials, including but not limited to: ethylene-vinyl acetate (EVA), expanded polypropylene (EPP), polyethylene (PE), polyurethane (PU), thermoplastic polyurethane (TPU), silicone, silicone gel, or the like. In some embodiments, flexible layers 28 may be made of a rigid material with less elasticity.

Foldable frame 22 may provide a rigid structure that electronic components of the facial wearable device 10 are coupled to as shown, for example, in FIGS. 10-12. Foldable frame 22 may include distal side 30 and proximal side 32. Proximal side 32 is opposite distal side 30 and adjacent to the user's head. Foldable frame 22 may further include right frame 34 and left frame 36 pivotally coupled together via hinge 38. Right frame 34 may be configured to rotate relative to left frame 36 around first axis 48 of hinge 38. Right frame 34 and left frame 36 may rotate relative to each other between an open configuration and a folded configuration (not shown). In some embodiments, hinge 38 may allow right frame 34 and left frame 36 to rotate to a partial open configuration at an angle that conforms to the user's head shape. For example, right frame 34 and left frame 36 may rotate so that right and left edges 76, 77 of eye cover 12 are closer together and provide a closer fit to a user with a smaller head diameter.

Hinge 38 may include a plurality of arms 45 that protrude from right and left frames 34, 36 on the proximal side 32 as shown, for example, in FIGS. 11 and 12. Hinge 38 may include a pin 47 that extends along first axis 48 through the protruding arms 45 to pivotally couple right and left frame 34, 36 together. In some embodiments, distal cover 20 includes an opening (not shown), parallel and adjacent to the first axis 48, to avoid the distal cover 20 stretching when the right and left frames 34, 36 are rotated into the folded configuration. Hinge 38 may include a hinge cover 46 to fill the opening of distal cover 20 in the folded configuration to protect hinge 38 from dirt, debris, or other foreign objects. Hinge cover 46 may extend outwardly away from the distal side of foldable frame 22 and couple to pin 47 as shown, for example, in FIG. 4.

The electronic components of facial wearable device 10 may be coupled to foldable frame 22. These electronic components may include, for example, processor 190, memory 192, battery 40, communication unit 42, and air pump 44 as shown, for example, in FIGS. 3, 4, and 10. Battery 40, communication unit 42, air pump 44, and other components may be coupled to foldable frame 22 and may be arranged on foldable frame to spread the respective weights of the components substantially equally across the facial wearable device 10 so that the facial wearable device is balanced when worn by the user. The facial wearable device may be determined to be weight balanced when the weights of the left and right sides of the device are within 10% of one another. Battery 40 may power all components of facial wearable device 10 including communication unit 42, air pump 44, and external stimuli devices that are part of the facial wearable device 10, which are described in more detail below. Battery 40 may couple to the distal side 30 of foldable frame 22 and may be recharged when power is connected to charging port 58.

Figure 31:
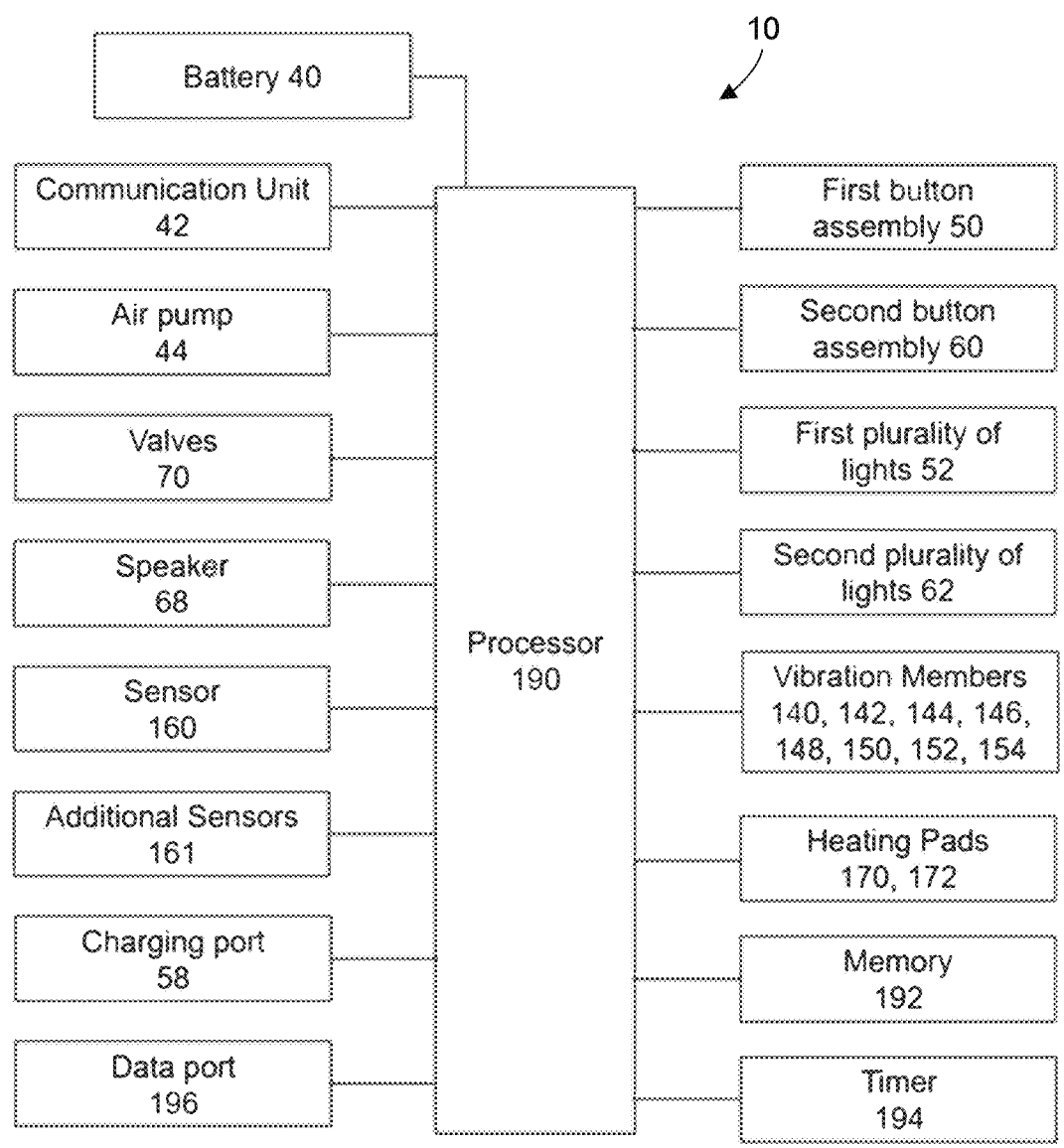
FIG. 31 is an example facial wearable device useful for implementing various embodiments of the present disclosure.

Processor 190 may control operation of some or all components of facial wearable device 10 including air pump 44, valves 70, first and second plurality of lights 52, 62, and external stimuli devices that are part of the facial wearable device 10, which are described in more detail below. Processor 190 may receive user inputs commands via one of the button assemblies 50, 60 or via a communication unit 42. In the illustrative embodiments in FIGS. 3, 4, and 10, processor 190 may couple and be located adjacent to battery 40. FIG. 31 shows an illustrative example of a block diagram of components of facial wearable device 10 according to some embodiments of the present invention. In the illustrated embodiment, the facial wearable device 10 may include processor 190 (processor 190 may also be a separate component). Facial wearable device 10 may also include a memory 192, timer 194, data port 196, a communication unit 42, and be coupled to battery 40 to provide power to the processor 190 and components coupled with the facial wearable device 10. These components may be operatively connected to one another to carry out the functionality of the processor 190. In other embodiments, one or more of these facial wearable device 10 components may be omitted, or one or more additional components may be added.

Processor 190 may be adapted to implement therapy presets and protocols stored in the memory 192 of the facial wearable device 10 as described in further detail below and shown in FIGS. 23-30. The processor 190 may also be capable of implementing analog or digital signal processing algorithms such as raw data reduction and filtering. For example, processor 190 may be configured to receive raw data from sensor 160 and process such data at the processor 190. The processor 190 is operatively connected to the battery 40, the memory 192, and the communication unit 42.

Battery 40 may be built into facial wearable device 10 or removable from the facial wearable device 10, and may be rechargeable or non-rechargeable. In some embodiments, the battery 40 may be recharged via charging port 58 or data port 196 by a cable attached to a charging source, such as a universal serial bus ("USB") FireWire, Ethernet, Thunderbolt, or headphone cable, attached to a personal computer.

Memory 192 may be adapted to store therapy presets, operation protocols, and user activity data. In some embodiments, memory 192 may store therapy presets and operation protocols used to implement aspects of the functionality of the facial wearable device 10 described in further detail below. In some embodiments, memory 192 may store raw data, recorded data, and/or calculated data. In some embodiments, memory 192 may act as a data storage buffer. Memory 192 may include both read only memory and random access memory, and may further include memory cards or other removable storage devices.

Timer 194 may be a clock that is capable of tracking absolute time and/or determining elapsed time during operation of a therapy preset or protocol. In some embodiments, timer 194 may be used to timestamp certain data records, such that the time that certain data was measured or recorded may be determined and various timestamps of various pieces of data may be correlated with one another.

Data port 196 may facilitate information transfer to and from the processor 190 and may be, for example, a USB port. In some exemplary embodiments, charging port 58 and data port 196 may be interchangeable and facilitate power transfer to battery 40, in order to a charge battery 40.

Figure 21:
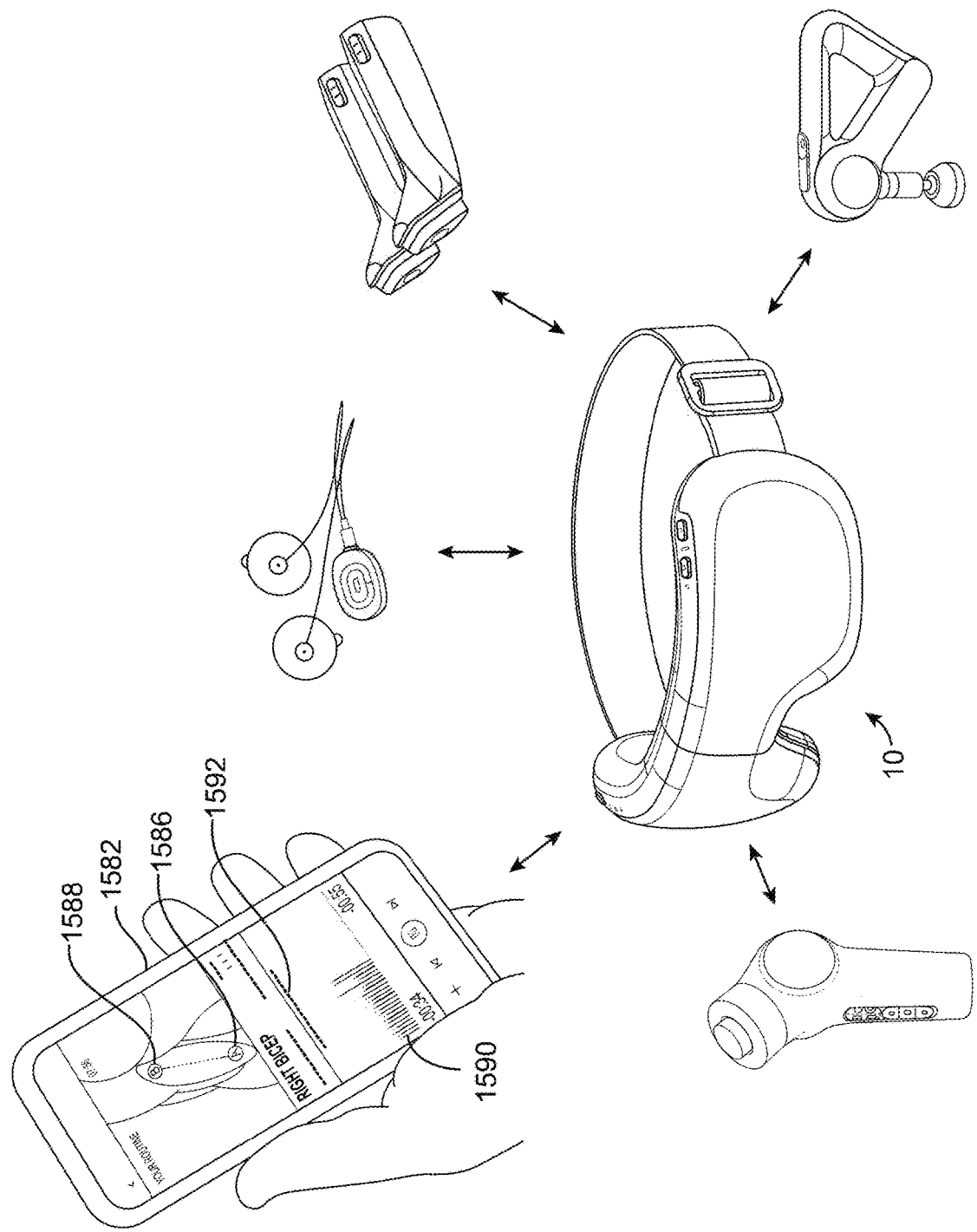
FIG. 21 illustrates an ecosystem of devices that may be in communication with a facial wearable device, according to an embodiment of the present disclosure.

Communication unit 42 may be configured to communicate directly or indirectly with an external device such as a user's mobile device or other ecosystem device as shown in FIG. 21. Communication unit 42 may communicate directly with the external device using a wireless connection such as Bluetooth or similar connection protocol. Communication unit 42 may provide device data such as selected mode, battery level, biometric data, and other similar parameters from the facial wearable device 10. Communication unit 42 may receive command inputs from a user such as mode select or external stimuli device intensity change.

Air pump 44 may provide an on-demand air supply to a plurality of air bladders in airbag layer 26. Air pump 44 may be fluidically coupled with valves 70 and air tubes 72. Valves 70 may control the flow of air provided to the plurality of bladders in airbag layer 26, and air tubes 72 may provide means to transfer the air supply from the air pump 44 to the airbag layer 26. As will be described in further detail below, each bladder of the plurality of bladders in airbag layer 26 may include a nozzle 103 that extends through the support layer 24 and foldable frame 22 and couples with the air tubes 72. In some embodiments, valves 70 may be configured to default in an open state, and close when activated to improve power consumption of battery 40.

In the illustrative embodiment in FIGS. 10-12, right frame 34 may include a first button assembly 50, first plurality of lights 52, battery recess 54, a plurality holes 56, and charging port 58. Battery recess 54 may be shaped and sized to accommodate battery 40. In some embodiments, battery recess 54 may include a grid pattern to improve venting of battery 40. First button assembly 50 may couple to right frame 34 along top edge 74. First button assembly 50 may include power and mode selector buttons. In the illustrative embodiment in FIG. 11, first button assembly 50 may include a single button that powers on the device and selects a preset mode of the facial wearable device depending on the duration of time the button is depressed. For example, a long press of first button assembly 50 may be configured to power on the facial wearable device 10. A short press of first button assembly 50 may be configured to select a user preferred preset mode of the facial wearable device 10 as will be further described below. In other embodiments, more than one button or non-button actuators may be used to control these features. First plurality of lights 52 may be positioned adjacent to first button assembly 50 and indicate a selected preset mode. In some embodiments, first plurality of lights 52 are LEDs. Charging port 58 may be located in a top corner, adjacent to top edge 74 and right edge 76 of eye cover 12 and be connected to battery 40 to recharge battery 40 as required. In some embodiments, charging port 58 may provide a data connection source such that an external device may be connected to facial wearable device 10 with a wired connection. Plurality of holes 56 may extend through right frame 34 to provide access and connection points for air tubes 72 and corresponding nozzles 103 of airbag layer 26.

In the illustrative embodiment in FIGS. 10-12, left frame 36 may include second button assembly 60, second plurality of lights 62, air pump recess 64, a plurality holes 66, and speaker 68. Air pump recess 64 may be shaped and sized to accommodate air pump 44. In some embodiments, air pump recess 64 may include a grid pattern to improve venting of air pump 44. Second button assembly 60 may couple to left frame 36 along top edge 74. Second button assembly 60 may include buttons to control the vibration and heating application settings of the external stimuli devices of facial wearable device 10. In the illustrative embodiment in FIG. 11, second button assembly 60 may include a vibration button and a heating button. Pressing each button for a selected duration of time may result in a different output from the button. For example, a short press of either the vibration button or the heating button may be configured to adjust an intensity of the corresponding function. A long press of either the vibration button of the heating button may be configured to start or stop the corresponding function. In other embodiments, more or less than two buttons or non-button actuators may be used to control these features. Second plurality of lights 62 may be positioned adjacent to second button assembly 60 and indicate an intensity level of the vibration or heating function. For example, at a first intensity level, the light 62 may illuminate a first color, at a second intensity level, the light 62 may illuminate a second color, and at a third intensity level, the light 62 may illuminate a third color. In some embodiments, more than three colors may be shown by the second plurality of lights 62. In some embodiments, second plurality of lights 62 are LEDs.

Speaker 68 may provide an audio signal to the user to indicate selection of a particular mode, function activated, and/or intensity level selected of a function. In some embodiments, speaker 68 may be an external user audio device, such as ear phones, or a mobile device speaker, wirelessly connected to the facial wearable device 10 via the communicate unit 42. In some embodiments, the facial wearable device 10 itself does not include a speaker 68. In some embodiments, when speaker 68 is present, it may provide external stimuli in categories such as composed musical tracks based on the predetermined combination of audio protocols, and/or a tagged musical track based on the associated mind-body goal category desired by the user. Additional audio stimuli protocols are described in U.S. patent application Ser. No. 17/933,423, to McVey et al., entitled "SYSTEM AND METHOD FOR ALTERING USER MIND-BODY STATES THROUGH EXTERNAL STIMULI," filed on the same day herewith, Sep. 19, 2022, and claiming priority to U.S. Provisional Patent Application Publication No. 63/352,005, which is incorporated herein by reference in its entirety.

Facial wearable device 10, and more specifically airbag layer 26 and flexible layers 28 of facial wearable device 10, may include one or more external stimuli devices in one or more of portions 80, 82, 86, 88, 92, 94, 96, 98 in the facial wearable device 10. In some embodiments, the placement of the one or more external stimuli devices may be configured to target specific facial locations to enhance performance and well-being of the user. The portions 80, 82, 86, 88, 92, 94, 96, 98 may be determined relative to the first axis 48 and a second axis 86 as shown, for example, in FIG. 20. First axis 48 may be approximately centered between the right and left edges 76, 77 and may define the pivot axis through which right frame 34 rotates relative to left frame 36. Left side portion 80 and right side portion 82 may be divided by first axis 48. Second axis 86 may extend between right edge 76 and left edge 77 approximately perpendicular to first axis 48. Second axis 86 may extend between edges 76, 77 at approximately a halfway height between top edge 74 at first axis 48, and apex 84 of bottom edge 75 at first axis 48. Upper side portion 88 and lower side portion 90 may be divided by second axis 86. Top-left portion 92, top-right portion 94, bottom-left portion 96, and bottom-right portion 98 may be defined and divided by first axis 48 and second axis 86 as shown, for example in FIG. 20. Top-left portion 92 may be located in left side portion 80 and upper side 88. Top-right portion 94 may be located in right side portion 82 and upper side 88. Bottom-left portion 96 may be located left side portion 80 and lower side 90. Bottom-right portion 98 may be located in right side portion 82 and lower side 90.

Facial wearable device 10, and more specifically airbag layer 26 may include one or more of inflatable bladders 104, 108, 112, 114, 116, 118, 128, 130 configured to individually or collectively inflate and deflate at a predefined rhythm or rhythms to provide stimulation, including massaging therapy, to acupoints or other portions of the face of the user. In various embodiments, the facial wearable device 10 may include eight, seven, six, five, four, three, two, or one inflatable bladders. As will be described in more detail below, one or more of inflatable bladders 104, 108, 112, 114, 116, 118, 128, 130 may be located in different portions 80, 82, 88, 90, 92, 94, 96, 98 of facial wearable device 10 and may be inflated individually or in combination such that different regions of a user's face may be stimulated simultaneously, selectively, and/or sequentially according to a preset mode or user defined preference. Facial wearable device 10 may operate air pump 44 via processor 190 to provide a controlled supply of air via one or more valves 70 and air tubes 72 to inflate one or more of the plurality of inflatable bladders 104, 108, 112, 114, 116, 118, 128, 130. In some embodiments, valves 70 may be in an open configuration such that activation of air pump 44 inflates all of the plurality of bladders 104, 108, 112, 114, 116, 118, 128, 130. In some embodiments, the valves 70 may be controlled by processor 190 between the open configuration and a closed configuration to direct air from the air pump 44 to selected bladders of the plurality of inflatable bladders 104, 108, 112, 114, 116, 118, 128, 130. In some embodiments, air pump 44 may be configured to supply a plurality of controlled air volumes such that air pump 44 and valves 70 may control inflation of selected bladders starting at different times. For example, a first control volume of air may begin inflating temple bladders 104, 108, and when temple bladders 104, 108 are approximately fifty percent inflated, a second control volume of air may begin to inflate eye bladders 112, 114, 116, 118.

In some embodiments, air pump 44 may activate for a predetermined time to fill one or more of the selected bladders of the plurality of inflatable bladders 104, 108, 112, 114, 116, 118, 128, 130 with a predetermined volume of air, and apply stimulation, such as pressure, to the user's face. Following activation of air pump 44 and inflating the one or more bladders of the plurality of inflatable bladders 104, 108, 112, 114, 116, 118, 128, 130, one or more of the bladders may deflate, removing the applied pressure from the user's face. Through control of air pump 44 and valves 70 for predetermined amounts of time, the plurality of inflatable bladders 104, 108, 112, 114, 116, 118, 128, 130 may inflate and deflate at selected rates to provide a rhythm of applied pressure to the face of the user. For example, the plurality of inflatable bladders 104, 108, 112, 114, 116, 118, 128, 130 may inflate and deflate to provide a rhythm of between approximately 10 to 20 inflations per minute. In some embodiments, one or more of the plurality of inflatable bladders 104, 108, 112, 114, 116, 118, 128, 130 may inflate and deflate to provide a rhythm of between approximately 5 to 30 inflations per minute. In some embodiments, one or more of the plurality of inflatable bladders 104, 108, 112, 114, 116, 118, 128, 130 may inflate and deflate to provide a rhythm of between approximately 12 to 17 inflations per minute. As will be described in detail below, such rhythms may allow the facial wearable device 10 to control respiratory rates of the user or adjust a mind-body state of the user.

In some embodiments, the air pump 44 may be controlled by processor 190 such that one or more of the bladders of the plurality of inflatable bladders 104, 108, 112, 114, 116, 118, 128, 130 inflate for about six seconds at a time. In some embodiments, the air pump 44 is controlled such that one or more of the bladders of the plurality of inflatable bladders 104, 108, 112, 114, 116, 118, 128, 130 inflate for about four seconds. In some embodiments, the air pump 44 controls one or more of the bladders of the plurality of inflatable bladders 104, 108, 112, 114, 116, 118, 128, 130 inflate for between about four seconds and about six seconds. In some embodiments, the air pump 44 is controlled such that one or more of the bladders of the plurality of inflatable bladders 104, 108, 112, 114, 116, 118, 128, 130 inflate for between about two seconds and about eight seconds. In some embodiments, one or more of inflatable bladders 104, 108, 112, 114, 116, 118, 128, 130 are configured to deflate in about one second. In some embodiments, one or more of inflatable bladders 104, 108, 112, 114, 116, 118, 128, 130 are configured to deflate in about two seconds. In some embodiments, one or more of inflatable bladders 104, 108, 112, 114, 116, 118, 128, 130 are configured to deflate in between about 0.5 seconds and about 4 seconds. In some embodiments, facial wearable device 10 may not include a pressure sensor, and inflation of one or more of bladders 104, 108, 112, 114, 116, 118, 128, 130 is based on air pump 44 activation time and volume of air supplied. In some embodiments, the air pump 44 may operate for a first inflation time to inflate one or more of bladders 104, 108, 112, 114, 116, 118, 128, 130, continue to operate for a hold inflation time to maintain the one or more bladders 104, 108, 112, 114, 116, 118, 128, 130 in a filled state, and deactivate for a deflate time so that the one or more bladders 104, 108, 112, 114, 116, 118, 128, 130 may deflate.

Figure 15:
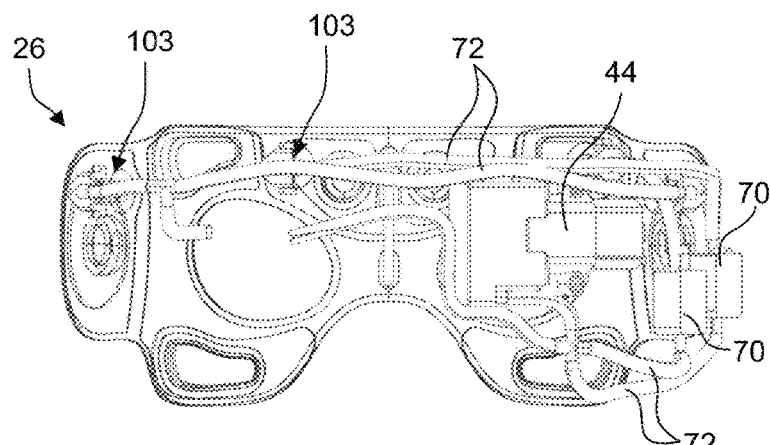
FIG. 15 illustrates a front view of an airbag layer of a facial wearable device showing an air pump, air valves, and air tubes, according to an embodiment of the present disclosure.
Figure 16:
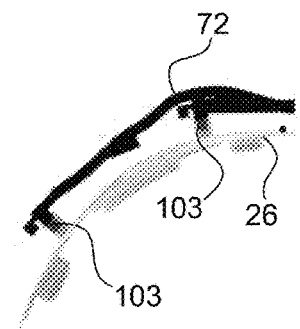
FIG. 16 illustrates a top view of an airbag layer of a facial wearable device showing connections between the air tubes and inflatable bladders in the airbag layer, according to an embodiment of the present disclosure.

Airbag layer 26 may be positioned over the temples of the user and may extend over the eyes and surrounding facial areas of the user. Left eye holes 100 and right eye hole 102 may extend through airbag layer 26 to provide recesses for the eyes of the user such that direct pressure is not applied on the eye lids and eye balls by the facial wearable device 10 as shown, for example, in FIG. 17. Left eye hole 100 may be positioned on left side portion 80 and right side hole 102 may be positioned on right side portion 82. Airbag layer 26 may further include one or more of right temple bladder 104, left temple bladder 108, first eye bladder 112, second eye bladder 114, third eye bladder, 116, fourth eye bladder 118, right center bladder 128, and left center bladder 130 as shown, for example, in FIG. 17. One or more of bladders 104, 108, 112, 114, 116, 118, 128, 130 may be positioned about airbag layer 26. In some embodiments, the one or more bladders are located to target different areas and acupoints around the user's face. Plurality of nozzles 103 may be coupled to each of bladders 104, 108, 112, 114, 116, 118, 128, 130 and may extend away from the user's face and through the support layer 24 and plurality of holes 56, 66 of foldable frame 22. Plurality of nozzles 103 may couple and connect with air tubes 72 such that the controlled air supply from air pump 44 may be supplied to one or more of bladders 104, 108, 112, 114, 116, 118, 128, 130 as shown, for example, in FIGS. 15 and 16.

Figure 20:
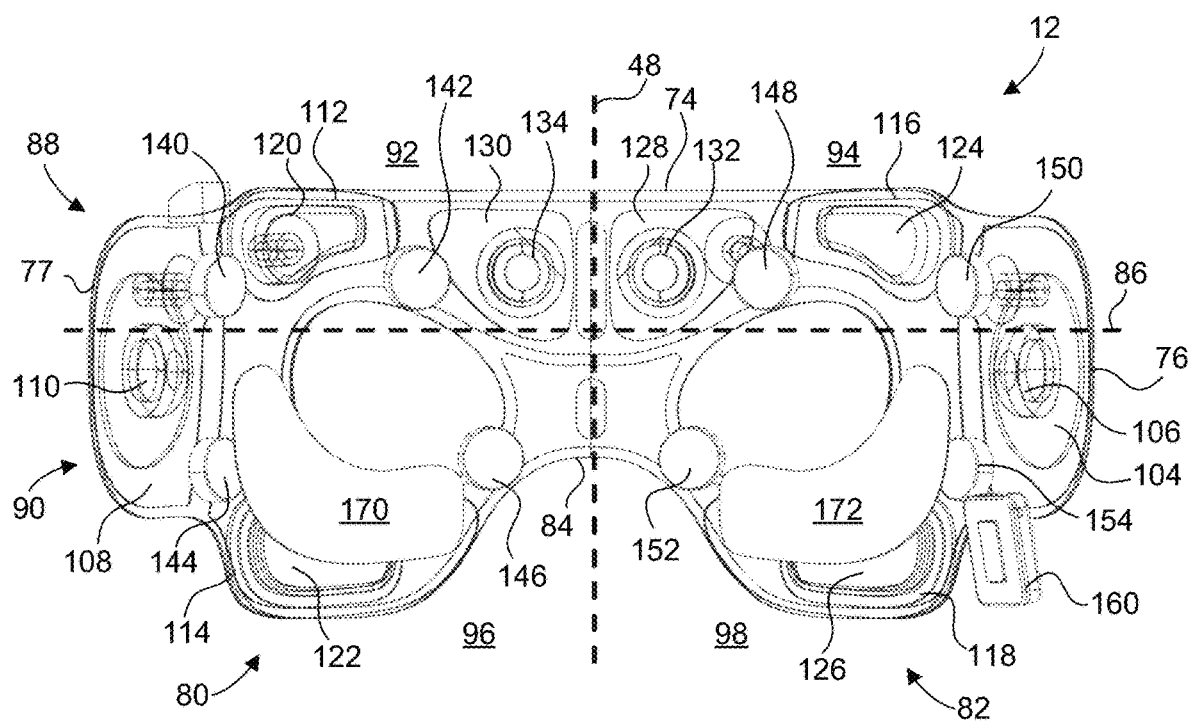
FIG. 20 illustrates a rear section view of a facial wearable device showing portions of the device where vibration motors, air bladders, and heating pads are located, according to an embodiment of the present disclosure.

In the illustrative embodiments in FIGS. 17 and 20, right temple bladder 104 may be positioned in right side portion 82 adjacent to right edge 76 of eye cover 12 such that right temple bladder 104 is positioned approximately adjacent to the user's right temple. In some embodiments, right temple bladder 104 may extend across top-right portion 94 and bottom-right portion 98. In some embodiments, right temple bladder 104 may be positioned in top-right portion 94 only. Left temple bladder 108 may be positioned in left side portion 80 adjacent to left edge 77 of eye cover 12 such that left temple bladder 108 may be positioned approximately adjacent to the user's left temple. In some embodiments, left temple bladder 108 may extend across top-left portion 92 and bottom-left portion 96. In some embodiments, left temple bladder 108 may be positioned in top-left portion 92 only. In some embodiments, right temple bladder 104 and left temple bladder 108 may be inflated separately by air pump 44. In the illustrative embodiment in FIG. 15, air tubes 72 may fluidically connect right temple bladder 104 and left temple bladder 108 such that air pump 44 inflates right temple bladder 104 and left temple bladder 108 simultaneously.

In the illustrative embodiment in FIG. 17, first eye bladder 112 may be positioned in top-left portion 92, second eye bladder 114 may be positioned in bottom-left portion 96, third eye bladder 116 may be positioned in top-right portion 94, and fourth eye bladder 118 may be positioned in bottom-right portion 98. In some embodiments, first eye bladder 112, second eye bladder 114, third eye bladder 116, and fourth eye bladder 118 may be configured to be inflated individually by air pump 44 and may be fluidically coupled to air pump 44 by individual valves 70 and air tubes 72 such that they may be controlled individually. In some embodiments first eye bladder 112 and second eye bladder 114 may be fluidically connected and configured to inflate and deflate simultaneously on left side 80 of eye cover 12. In some embodiments third eye bladder 116 and fourth eye bladder 118 may be fluidically connected and configured to inflate and deflate simultaneously on right side 82 of eye cover 12. In the illustrative embodiment in FIG. 17, first eye bladder 112, second eye bladder 114, third eye bladder 116, and fourth eye bladder 118 may be fluidically coupled and configured to inflate and deflate simultaneously.

In the illustrative embodiment in FIG. 17, left-center bladder 130 may be positioned in top-left portion 92 and right-center bladder 128 may be positioned in top-right portion 94. In some embodiments, left-center bladder 130 and right-center bladder 128 may be configured to be inflated individually by air pump 44 and may be fluidically coupled to air pump 44 by individual valves 70 and air tubes 72 such that they are controlled individually. In some embodiments left-center bladder 130 and right-center bladder 128 may be fluidically connected and configured to inflate and deflate simultaneously.

Facial wearable device 10, and more specifically airbag layer 26, may further include one or more of right temple pad 106, left temple pad 110, first eye pad 120, second eye pad 122, third eye pad 124, fourth eye pad 126, right center pad 132, and left center pad 134 as shown, for example, in FIG. 17. In various embodiments, the facial wearable device 10 may include eight, seven, six, five, four, three, two, or one pads. One of more of pads 106, 110, 120, 122, 124, 126, 132, 134 may provide a cushion, such as a soft pillow, that may focus the inflation pressure on a particular location of the user's face. One or more of pads 106, 110, 120, 122, 124, 126, 132, 134 may be coupled to corresponding surfaces of each of bladders 104, 108, 112, 114, 116, 118, 128, 130. In some embodiments, one or more of pads 106, 110, 120, 122, 124, 126, 132, 134 may be generally circular, oval, tear-drop shaped, or other similar contoured shape. In the illustrative embodiment in FIG. 17, right temple pad 106, left temple pad 110, right-center pad 128 and left-center pad 130 may be generally circular, and first, second, third, and fourth eye pads 120, 122, 124, 126 may have contoured profiles that approximately follow respective top and bottom edge 74, 75 and left and right eye hole 100, 102 curvatures.

Flexible layers 28 may include external stimuli devices to provide vibration and/or heat to the facial area of the user. Flexible layers 28 may include first foam layer 136 adjacent to airbag layer 26 and second foam layer 138 may be positioned substantially between first foam layer 136 and proximal cover 21. First and second foam layers 136, 138 may be made from soft materials, such as protein fabric, that are comfortable for the user and may approximately mold to the facial profile of the user. Vibration and heating devices may be coupled with first foam layer 136 such that second foam layer 138 may act as a buffer to prevent direct contact between the vibration and heating devices with the users face.

Facial wearable device 10, and more specifically first foam layer 136 may include one or more of first vibration member 140, second vibration member 142, third vibration member 144, fourth vibration member 146, fifth vibration member 148, sixth vibration member 150, seventh vibration member 152, and eighth vibration member 154 as shown, for example, in FIGS. 18 and 19. In various embodiments, the facial wearable device 10 may include eight, seven, six, five, four, three, two, or one vibration members. One or more of the vibration members 140, 142, 144, 146, 148, 150, 152, 154 may be controlled by processor 190 and may provide a vibrating pulse at a particular location that can be felt by the user. One or more of the plurality of vibration members 140, 142, 144, 146, 148, 150, 152, 154 may be distributed across the first foam layer in at least one of the eye cover portions 80, 82, 88, 90, 92, 94, 96, 98. In the illustrative embodiment in FIG. 18, first vibration member 140 and second vibration member 142 may be positioned in top-left portion 92, third vibration member 144 and fourth vibration member 146 may be positioned in bottom-left portion 96, fifth vibration member 148 and sixth vibration member 150 may be positioned in top-right portion 94, and seventh vibration member 152 and eighth vibration member 154 may be positioned in bottom-right portion 98. In some embodiments, at least one vibration members may be positioned in each of the portions 92, 94, 96, 98. In some embodiments, at least four vibration members may be positioned in each of the left and right side portions 80, 82. In some embodiments, at least four vibration members may be positioned in each of the upper side portion 88 and the lower side portion 90. In some embodiments, facial wearable device 10 may include more than eight more vibration members.

One or more of the plurality of vibration members 140, 142, 144, 146, 148, 150, 152, 154 may be controlled individually, by processor 190, in their respective portions 80, 82, 88, 90, 92, 94, 96, 98 such that a customizable routine can be created to target areas of the user's face simultaneously or sequentially in a pattern. Alternatively, in some other embodiments, one or more subsets of vibration members 140, 142, 144, 146, 148, 150, 152, 154 may be controlled together as individual subsets, or all may be controlled together. One or more of the plurality of vibration members 140, 142, 144, 146, 148, 150, 152, 154 may be activated for a predefined duration of time or intensity. For example, vibration members 140, 142, 148, 150 may be positioned in upper side portion 88 and may be activated for a first time and first intensity, followed by vibration members 144, 146, 152, 154 positioned in lower side portion 90 that may be activated for a second time and second intensity. Such control of the vibration members may, for example, mimic a heartbeat rhythm through alternating vibration members with different activation durations and intensities. In some embodiments, vibration members may be controlled in pairs in approximately complimentary locations across the first axis 48. For example, in the illustrative embodiment in FIG. 18, first vibration member 140 may operate together with sixth vibration member 150, and second vibration member 142 may operate together with fifth vibration member 148. Additional exemplary vibrating patterns according to predefined presets and protocols are shown in FIGS. 23 and 24.

In some embodiments, processor 190 may control one or more of the vibration members 140, 142, 144, 146, 148, 150, 152, 154 to operate together in a wave pattern. During operation of the wave pattern, the voltage to one or more of the vibration members 140, 142, 144, 146, 148, 150, 152, 154 may be increased between zero voltage and a maximum voltage over a first predetermined amount of time, followed by ramping down from the maximum voltage to zero voltage over a second predetermined amount of time. As such, the vibration intensity of each of the plurality of vibration members may increase over the first predetermined amount of time between zero vibration to maximum vibration intensity, and then may decrease back to zero vibration intensity over the second predetermined amount of time. By operating one or more of the plurality of vibration members 140, 142, 144, 146, 148, 150, 152, 154 together, a common wave of vibration intensity may be felt by the user across the facial wearable device 10. In some embodiments, the first predetermined amount and the second predetermined amount of time may be approximately three seconds. In some embodiments, the first predetermined amount of time and the second predetermined amount of time may be shorter than three seconds but greater than 0.5 seconds. In some embodiments, the first predetermined amount of time and the second predetermined amount of time may be longer than three seconds and less than ten seconds. In some embodiments, the first predetermined amount of time and the second predetermined amount of time may be different. In some embodiments, the voltage increase and decrease to one or more of the vibration members 140, 142, 144, 146, 148, 150, 152, 154 may be one of a linear, sinusoidal, or other pattern.

First foam layer 136 further includes one or more sensors 160 to collect biometric data from the user. While collection of data via a single sensor may be discussed herein, data collection may be similarly achieved by additional sensors 161 in some embodiments. In some embodiments, sensor 160 may be one of a heart rate sensor, an eye motion sensor, a microphone, a blood pressure sensor, an electroencephalogram sensor, a muscle activity sensor, an electrocardiography sensor, a photoplethysmography sensor, an electroencephalograph sensor, an accelerometer, a pressure sensor, a respiration sensor, and/or a touch sensor. For example, a heart rate sensor may sense a user's heart rate and be used to adjustably control one or more of the plurality of vibration members 140, 142, 144, 146, 148, 150, 152, 154 as part of a heart control protocol therapy. In another example, a respiration sensor may sense a respiration rate of a user and be used to adjustably control one or more of the plurality of vibration members 140, 142, 144, 146, 148, 150, 152, 154 and/or adjustably inflate one or more of the plurality of bladders 104, 108, 112, 114, 116, 118, 128, 130. In another example, a temperature sensor may sense a user's body temperature and increase or decrease a heating level supplied by one or more of heating pads 170, 172.

Sensor 160 may extend away from first foam layer 136 and through sensor recess 180 formed in second foam layer 138 so that sensor 160 may contact the user's face and skin. The sensor may be mounted on a flexible substrate so that it can flex and achieve close contact with the skin for optimal performance. In the illustrative embodiment in FIG. 18, sensor 160 may be positioned in bottom-right portion 98. In some embodiments, sensor 160 may be positioned in one of top-left portion 92, top-right portion 94, or bottom-left portion 96. In some embodiments, sensor 160 may be positioned on first foam layer 136 so that it is approximately adjacent to the user's cheek. Data collected by sensor 160 may be used in a dynamic device protocol to modify the output of the external stimuli devices based on the biometric data received as described in further detail below.

First foam layer 136 may further include one or more heating pads, such as first heading pad 170 and second heating pad 172 configured to heat a facial region of the user. In other embodiments, three or four heating pads may be used. One or more of the heating pads, such as first heating pad 170 and second heating pad 172 may be operated independently or simultaneously by processor 190. For example, heating pads 170, 172 may be controlled to increase or decrease the heat output. In some embodiments, heating pads 170, 172 may have at least two different heating levels. In the preset embodiments described below and shown in FIGS. 26-28 the heating pads 170, 172 may have three different heating levels: low, medium, and high. The low heating level of heating pads 170, 172 may be approximately 37 degrees Celsius, between 35 and 40 degrees, or between 30 and 45 degrees. The medium heating level of heating pads 170, 172 may be approximately 40 degrees Celsius, between 35 and 45 degrees, or between 30 and 50 degrees. The high heating level of heating pads 170, 172 may be approximately 42 degrees Celsius, or between 40 and 50 degrees. For each of the heating levels, the plurality of lights 62 may illuminate a corresponding color to indicate to the user the heating level selected.

In the illustrative embodiments in FIGS. 18 and 19, first heating pad 170 and second heating pad 172 may be arranged substantially symmetrically on first foam layer 136 across first axis 48. First heating pad 170 may be positioned in bottom-left portion 96 and second heating pad 172 may be positioned in bottom-right portion 98 such that each of the heating pads 170, 172 target a lower perimeter portion of the user's eye. In some embodiments, first heating pad 170 may be substantially positioned in bottom-left portion 96 and extend into top-left portion 92, and second heating pad 172 may be substantially positioned in bottom-right portion 98 and extend into top-right portion 94. In some embodiments, two or more heating pads are coupled to first foam layer 136. In some embodiments, heating pads 170, 172 may be positioned in top-left and top-right portions 92, 94. In some embodiments, at least two heating pads may be positioned on each of the left and right side portions 80, 82. In some embodiments, heating pads may be positioned in similar location to other external stimuli such as vibration members or airbag bladders.

An illustrative embodiment of a facial wearable device 10 connected ecosystem is shown in FIG. 21. Facial wearable device 10 may be capable of wirelessly connecting to and communicating with at least one other electronic device, including but not limited to a physical stimuli device such as a massage device, or a mobile device. Facial wearable device 10 may communicate with another device to share data, such as biometric data collected by sensor 160 or user stored presets. Facial wearable device may also receive data from other device in the ecosystem such as user inputs from the mobile device, biometric data from another sensor on a different device, or other therapeutic treatments being carried out previously or concurrently with a different device. Facial wearable device 10 may receive data from and communicate with other devices such as, for example, heart rate, HRV, respiratory rate, blood oxygen saturation, EEG, body temperature, physical activity, sleep time, time of device use, type of device used, speeds used, force levels applied, attachments used, battery durations, geo location, gender, and age data.

Connected physical stimuli devices can be used to provide physical external stimuli when altering a user mind-body state to other parts of the body. Physical stimuli devices can be any device capable of providing an external stimulus to the surface of a user's body. Physical stimuli devices can be a wearable garment, a compression device, a percussive massage device, a vibration therapy device, a vibration therapy garment, a massage table, a massage pillow, a massage chair, a muscle stimulator, a blanket, a watch, a seating cover, or a standing mat.

Suitable connected physical stimuli devices within the ecosystem may be, for example, percussive massage devices, such as those disclosed in U.S. Patent App. Pub. Nos. 2021/0244611, 2021/0022955, and 2020/0352821; vibration therapy devices, such as those disclosed in U.S. Patent App. Pub. No. 2021/0128399; electrical muscle stimulation devices, such as those disclosed in U.S. Pat. No. 10,881,849; percussive massage devices, such as those disclosed in U.S. Patent App. Pub. No. 2021/0401663A1; pneumatic compression devices, such as those disclosed in U.S. Patent App. Pub. No. 2022/0241137; or eye massage devices, such as those disclosed in U.S. Provisional Patent App. No. 63/335,540. Each of the above mentioned patents, publications, and applications are incorporated herein by reference in their entireties, except for any definitions, subject matter disclaimers or disavowals, and except to the extent that the incorporated material is inconsistent with the express disclosure herein, in which case the language in this disclosure controls.

Physical stimuli devices can be a device providing an external stimulus that is at a certain frequency (e.g., vibrations per minute), amplitude, or torque. As described above, physical stimuli devices can be used to provide physical external stimuli that corresponds to certain physical protocols, including binaural rhythms, a device to be used, and specifications of the mechanical motion of the device (e.g., frequency, amplitude, torque, revolutions per minute, inflations per minute, percussions per minute, or vibrations per minute).

Figure 22:
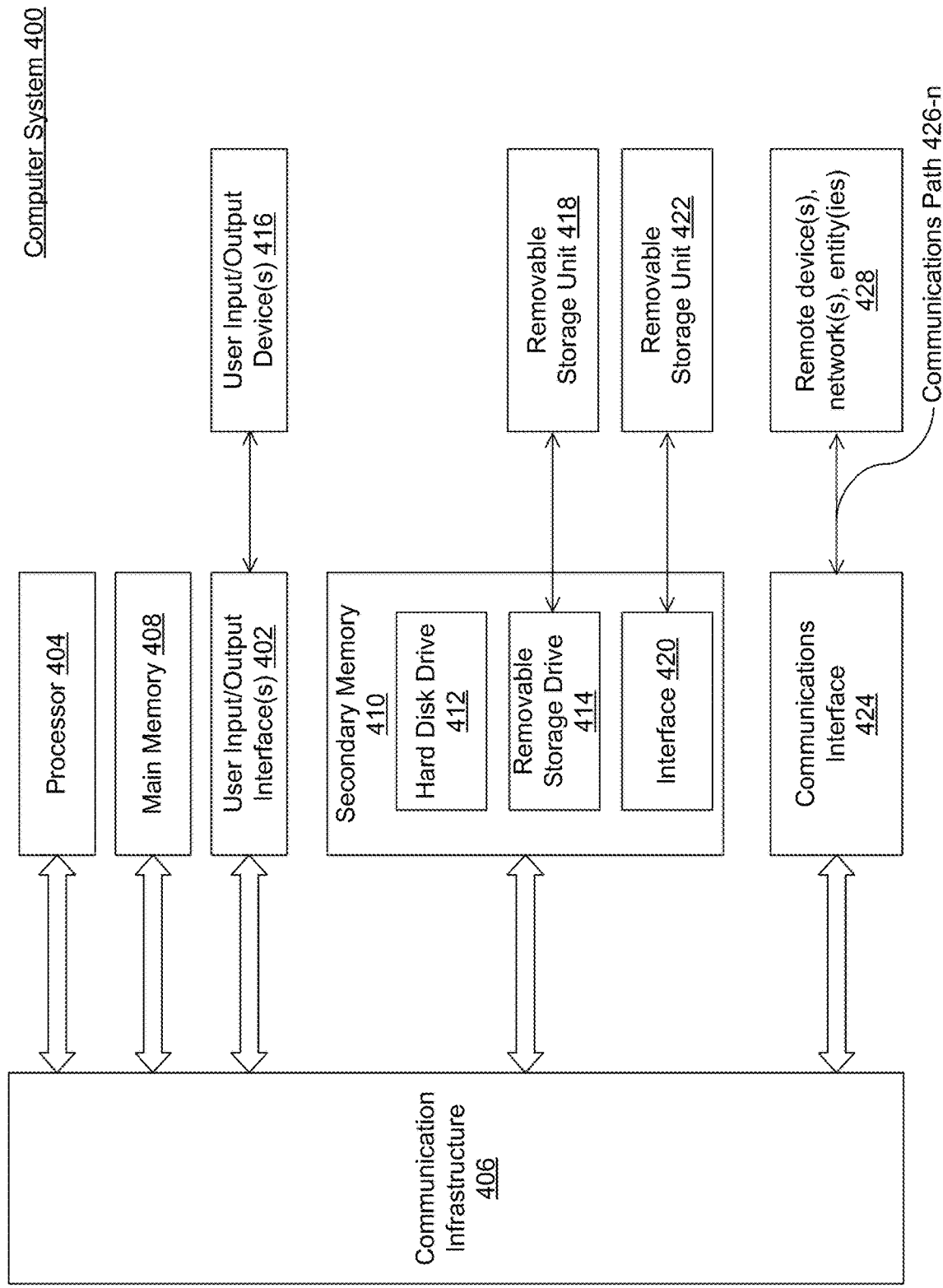
FIG. 22 illustrates a block diagram of an example computer system useful for implementing various aspects of the present disclosure.
Figure 29:
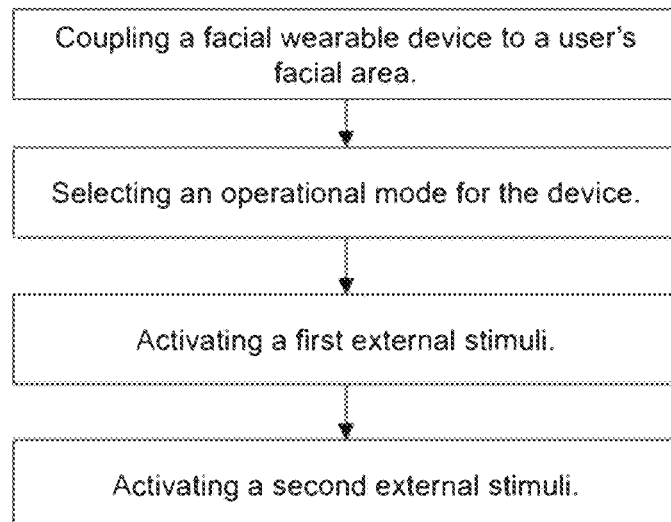
FIG. 29 is a flow chart showing the steps of a method for operating a facial wearable device and activating external stimuli, according to an embodiment of the present disclosure.
Figure 30:
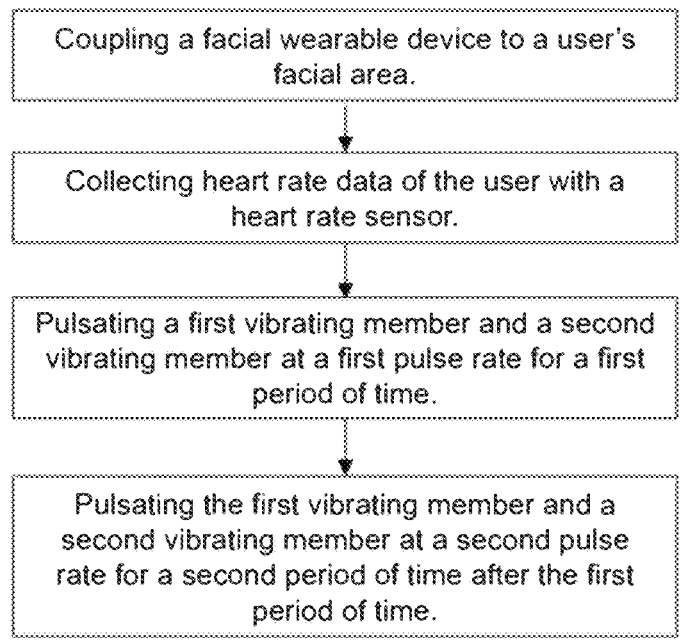
FIG. 30 is a flow chart showing the steps of a method for operating a facial wearable device and activating external stimuli in response to a user's biometric data, according to an embodiment of the present disclosure.

Various embodiments can be implemented, for example, using one or more computer systems, such as computer system 400 shown in FIG. 22. Computer system 400 can be used, for example, to implement a system for altering a user mind-body state through external stimuli described above. For example, computer system 400 can provide a multi-sensory experience with personalized external stimuli (e.g., audio and/or physical stimuli). Computer system 400 can be any computer capable of performing the functions described herein.

Computer system 400 can be any well-known computer capable of performing the functions described herein.

Computer system 400 includes one or more processors (also called central processing units, or CPUs), such as a processor 404. Processor 404 is connected to a communication infrastructure or bus 406.

One or more processors 404 can each be a graphics processing unit (GPU). In an embodiment, a GPU is a processor that is a specialized electronic circuit designed to process mathematically intensive applications. The GPU can have a parallel structure that is efficient for parallel processing of large blocks of data, such as mathematically intensive data common to computer graphics applications, images, videos, etc.

Computer system 400 also includes user input/output device(s) 416, such as monitors, keyboards, pointing devices, etc., that communicate with communication infrastructure 406 through user input/output interface(s) 402.

Computer system 400 also includes a main or primary memory 408, such as random access memory (RAM). Main memory 408 can include one or more levels of cache. Main memory 408 has stored therein control logic (i.e., computer software) and/or data.

Computer system 400 can also include one or more secondary storage devices or memory 410. Secondary memory 410 can include, for example, a hard disk drive 412 and/or a removable storage device or drive 414. Removable storage drive 414 can be a floppy disk drive, a magnetic tape drive, a compact disk drive, an optical storage device, tape backup device, and/or any other storage device/drive.

Removable storage drive 414 can interact with a removable storage unit 418. Removable storage unit 418 includes a computer usable or readable storage device having stored thereon computer software (control logic) and/or data. Removable storage unit 418 can be a floppy disk, magnetic tape, compact disk, DVD, optical storage disk, and/any other computer data storage device. Removable storage drive 414 reads from and/or writes to removable storage unit 418 in a well-known manner.

According to an exemplary embodiment, secondary memory 410 can include other means, instrumentalities or other approaches for allowing computer programs and/or other instructions and/or data to be accessed by computer system 400. Such means, instrumentalities or other approaches can include, for example, a removable storage unit 422 and an interface 420. Examples of the removable storage unit 422 and the interface 420 can include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 400 can further include a communication or network interface 424. Communication interface 424 enables computer system 400 to communicate and interact with any combination of remote devices, remote networks, remote entities, etc. (individually and collectively referenced by reference number 428). For example, communication interface 424 can allow computer system 400 to communicate with remote devices 428 over communications path 426, which can be wired, and/or wireless, and which can include any combination of LANs, WANs, the Internet, etc. Control logic and/or data can be transmitted to and from computer system 400 via communication path 426.

In an aspect, a tangible, non-transitory apparatus or article of manufacture comprising a tangible, non-transitory computer useable or readable medium having control logic (software) stored thereon is also referred to herein as a computer program product or program storage device. This includes, but is not limited to, computer system 400, main memory 408, secondary memory 410, and removable storage units 418 and 422, as well as tangible articles of manufacture embodying any combination of the foregoing. Such control logic, when executed by one or more data processing devices (such as computer system 400), causes such data processing devices to operate as described herein.

In some embodiments, computer system 400 may be included in facial wearable device 10. In some embodiments computer system 400 may be included in an external device such as a mobile phone, tablet, or the other devices shown in FIG. 21.

Exemplary Method of Heart Rate Control

According to some embodiments, the actuation of one or more of the vibration members 140, 142, 144, 146, 148, 150, 152, 154 may provide haptic physical feedback to a user to aid the user to achieve a desired heart rate. For example, the user may have an elevated heart rate due to anxiety, and wish to lower their heart rate to help feel relaxed. Facial wearable device 10 may control one or more of vibration members 140, 142, 144, 146, 148, 150, 152, 154 at a determined pulse rate based on the heart rate of the user received at the sensor

160. The determined pulse rate may have an upper treatment limit of about 60 pulses per minute and a lower treatment limit of about 24 pulses per minute. In some embodiments, the upper treatment limit may be about 120 pulses per minute and the lower treatment limit may be about 10 pulses per minute. In some embodiments, the upper treatment limit may be about 80 pulses per minute and the lower treatment limit may be about 20 pulses per minute. In some embodiments, the upper treatment limit may be about 100 pulses per minute and the lower treatment limit may be about 40 pulses per minute.

Facial wearable device 10 may operate one or more of the vibration members 140, 142, 144, 146, 148, 150, 152, 154 in pairs, such that a vibration member 140, 142, 148, 150 positioned in the upper side portion 88 is paired with a vibration member 144, 146, 152, 154 in the lower side portion 90. Further, pairs of vibration members (140/144, 142/146) on left side 80 may be paired with pairs of vibration members (150/154), 148/152 on right side 82. For example, first vibration member 140 and sixth vibration member 150, positioned in top-left portion 92 and top-right portion 94 respectively, may be paired with third vibration member 144 and eighth vibration member 154, positioned in bottom-left portion 96 and bottom-right portion 98.

Paired vibration members may be configured to operate at different intensity levels such that the vibration member 140, 142, 148, 150 in the upper side portion 88 pulse at a greater intensity than the vibration member 144, 146, 152, 154 in the lower side portion 90, or vice versa. In addition, the pairs of vibration members may pulsate sequentially such that the vibration member 140, 142, 148, 150 in the upper side portion 88 pulses before the vibration member 144, 146, 152, 154 in the lower side portion 90, or vice versa. The sequential pulsing and differing intensity levels between each pair of vibration members may mimic a sinus rhythm of a human heartbeat.

The user may select a heart control function of the facial wearable device 10 for a predetermined treatment period, such as, for example, fifteen minutes. In other embodiments, the treatment period may be, for example, between ten and twenty minutes, between five and twenty-five minutes, or between one and thirty minutes. Each treatment period may be divided up into a plurality of smaller dynamic periods where the pulse rate may be updated based on the heart rate of the user. For a first dynamic period, sensor 160 may detect the heart rate of the user. Facial wearable device 10 may operate at least one of the pairs of vibration members at a first pulse rate equal to a first percentage of the heart rate of the user. If the first pulse rate is determined to be greater than the upper treatment limit, facial wearable device 10 may operate the at least one of the pairs of vibration members at the upper treatment limit (e.g. about 60 pulses per minute). In the illustrative embodiment in FIG. 23, the first percentage is 100%.

For a second dynamic period, following the first dynamic period, sensor 160 may detect the heart rate of the user and facial wearable device 10 may operate at least one of the pairs of vibration members at a second pulse rate equal to a second percentage of the heart rate of the user. If the second pulse rate is determined to be greater than the upper treatment limit, facial wearable device 10 may operate the at least one of the pairs of vibration members at the upper treatment limit (e.g. about 60 pulses per minute). The second percentage is less than the first percentage. For example, the second percentage may be 97%. Facial wearable device 10 continues to lower the pulse rate by implementing lowering percentages for following dynamic periods until the treatment period is over, a desired heart rate of the user is achieved, or the pulse rate is equal to the lower treatment limit (e.g. about 24 pulses per minute). If the desired heart rate of the user is achieved before the end of the treatment period, facial wearable device 10 may maintain a pulse rate of the vibration members equal to the desired heart rate.

For example, if a user has a heart rate of 88 beats per minute and wishes to lower their heart rate to 50 beats per minute, one or more of the pairs of vibration members 140/144, 150/154, 142/146, 148/152 may provide haptic feedback in the first minute of the treatment to mimic a heart rate of about 60 beats per minute (the upper treatment limit). If in the second minute of the treatment, the user's heart rate has dropped to 60 beats per minutes, one or more of the pairs of vibration members 140/144, 150/154, 142/146, 148/152 may provide haptic feedback to mimic a heart rate of 58 beats per minute (97% of user's heart rate).

In another example, if a user has a heart rate of 54 beats per minute and wishes to lower their heart rate to 45 beats per minute, one or more of the pairs of vibration members 140/144, 150/154, 142/146, 148/152 may provide haptic feedback in the first minute of the treatment to mimic a heart rate of about 54 beats per minute (100% of user heart rate). If in the second minute of the treatment, the user's heart rate has dropped to 49 beats per minutes, the pairs of vibration members 140/144, 150/154, 142/146, 148/152 may provide haptic feedback to mimic a heart rate of 48 beats per minute (97% of user's heart rate).

In another operational mode, facial wearable device 10 may be configured to increase the heart rate. For example, the user may have a lowered heart rate due to sleeping, resting, or otherwise being in a relaxed state and desire to increase their heart rate to become focused or energized. In the energize or focus operational mode, for a first dynamic period, sensor 160 may detect the heart rate of the user. Facial wearable device 10 may operate at least one of the vibrating pairs at a first pulse rate equal to a first percentage of the heart rate of the user. If the first pulse rate is determined to be lower than the lower treatment limit, facial wearable device 10 may operate the at least one of the vibrating pairs at the lower treatment limit. In the illustrative embodiment in FIG. 23, the first percentage is 100%. For a second dynamic period, sensor may detect the heart rate of the user and facial wearable device 10 may operate at least one of the vibrating pairs at a second pulse rate equal to a second percentage of the heart rate of the user. The second percentage is greater than the first percentage. For example, the second percentage may be about 103%. Facial wearable device 10 may continue to increase the pulse rate by using increasing the percentages for following dynamic periods.

For example, if a user has a heart rate of 40 beats per minute and wishes to increase their heart rate to 50 beats per minute, one or more of the pairs of vibration members 140/144, 150/154, 142/146, 148/152 may provide haptic feedback in the first minute of the treatment to mimic a heart rate of 40 beats per minute. If in the second minute of the treatment, the user's heart rate has increased to 44 beats per minutes, one or more of the pairs of vibration members 140/144, 150/154, 142/146, 148/152 may provide haptic feedback to mimic a heart rate of 45 beats per minute (103% of user's heart rate).

In some embodiments, the facial wearable device 10 may include five programmable zones such as, for example, focus, energize, relax, inspire, and sleep. For each of said programmable zones, the facial wearable device 10 may provide a signal to one or more of vibration members 140, 142, 144, 146, 148, 150, 152, 154 to provide haptic feedback within a range of heart rates that correspond to each of the programmed zones and user conscious states. In some embodiments, indicia such as a color may be associated with each programmable zone.

In some embodiments, a method for providing heart rate information about a user, and/or providing biofeedback to the user, may include defining a plurality of heart rate zones as ranges of beats per minute of the user. In some embodiments, the zones may be defined by parameters other than heart rate ranges. In some embodiments, the method may include determining upper and lower limits for heart rate zones, and/or associating a color with each of said heart rate zones. In some embodiments, the method may include receiving heart rate information from the sensor 160, and/or providing biofeedback to the user of the facial wearable device 10 by providing a signal to one or more of the plurality of vibration members 140, 142, 144, 146, 148, 150, 152, 154 to vibrate in a way that that corresponds to each of the intended zones and user consciousness states. In some embodiments, the method may also include initiating a display or other visual indicia on the facial wearable device 10 or a separate device (e.g., a phone) in response to receiving the heart rate information from the user and/or providing biofeedback to the user. In some embodiments, a color of the display or other visual indicia corresponds with the color associated with one of said heart rate zones.

Exemplary Method of Respiration Rate Control

In some embodiments, the actuation of the one or more vibration members 140, 142, 144, 146, 148, 150, 152, 154 may be configured to mimic a respiration rate of a user, instead of their heart rate, to aid the user in controlling their respiration rate. In some embodiments, air pump 44 may be operated to inflate or deflate one or more of the bladders 104, 108, 112, 114, 116, 118, 128, 130 to mimic either a desired increase or decrease of respiration rate of the user. In some embodiments, one or more of vibration members 140, 142, 144, 146, 148, 150, 152, 154 may operate concurrently with one or more of the bladders 104, 108, 112, 114, 116, 118, 128, 130 to mimic either a desired increase or decrease of respiration rate of the user. In some embodiments, sensor 160 may be configured to detect a respiration rate of the user and adjust a pulsing operation of the vibration members and inflation operation of the plurality of bladders to aid the user in controlling their respiration rate.

The user may select a respiration control function of the facial wearable device 10 for a predetermined treatment period, such as, for example, fifteen minutes. In other embodiments, the treatment period may be, for example, between ten and twenty minutes, between five and twenty-five minutes, or between one and thirty minutes. Each treatment period may be divided up into a plurality of smaller dynamic periods where the inflation rate is updated based on the respiration rate of the user. For a first dynamic period, sensor 160 may detect the respiration rate of the user. Facial wearable device 10 may operate at least one of the pairs of vibration members at a first pulse rate and at least one of the plurality of bladders at a first inflation rate equal to a first percentage of the respiration rate of the user. For a second dynamic period, following the first dynamic period, sensor 160 may detect the respiration rate of the user and facial wearable device 10 may operate at least one of the pairs of vibration members at a second pulse rate and at least one of the plurality of bladders at a second inflation rate equal to a second percentage of the respiration rate of the user. Facial wearable device 10 continues to increase or decrease the pulse rate and inflation rate by implementing increasing or decreasing percentages of the detected respiration rate for following dynamic periods until the treatment period is over or a desired respiration rate of the user is achieved. In some embodiments, facial wearable device 10 may only operate at least one of the pairs of vibration members at a varying pulse rates related to the respiration rate of the user over sequential dynamic periods until the treatment period is over or a desired respiration rate of the user is achieved. In some embodiments, facial wearable device 10 may only operate at least one of the plurality of bladders at varying inflation rates related to the respiration rate of the user over sequential dynamic periods until the treatment period is over or a desired respiration rate of the user is achieved.

In some embodiments, the facial wearable device 10 may include five programmable zones such as focus, energize, relax, inspire, and sleep. For each of said programmable zones, the facial wearable device 10 may provide a signal to the air pump 44 and valves 70 to inflate and deflate the plurality of bladders 104, 108, 112, 114, 116, 118, 128, 130 within a range of breathing patterns that correspond to each of the programmed zones and user conscious states. In some embodiments, indicia such as a color may be associated with each programmable zone.

In some embodiments, a method for providing respiration rate information about a user, and/or providing biofeedback to the user, may include defining a plurality of respiration rate zones as ranges of breaths per minute of the user. In other embodiments, the zones may be defined by parameters other than respiration rate ranges. In some embodiments, the method may include determining upper and lower limits for respiration rate zones, and/or associating a color with each of said respiration rate zones. In some embodiments, the method may include receiving respiration rate information from the sensor 160 or other device in the ecosystem shown in FIG. 21, and/or providing biofeedback to the user of the facial wearable device 10 by providing a signal to the air pump 44 and valves 70 to inflate and deflate one or more of bladders 104, 108, 112, 114, 116, 118, 128, 130 within a range of breathing patterns that correspond to each of the intended zone and user consciousness state. In some embodiments, the method may also include initiating a display or other visual indicia on the facial wearable device 10, for example via the first plurality of lights 52, or a separate device (e.g., a phone) in response to receiving the respiration rate information from the user and/or providing biofeedback to the user. In some embodiments, a color of the display or other visual indicia corresponds with the color associated with one of said respiration rate zones.

Exemplary Device Preset Functions

In some embodiments, facial wearable device 10 may be configured to provide a plurality of preset functions to the user using one or more of vibration members 140, 142, 144, 146, 148, 150, 152, 154, one or more of the plurality of bladders 104, 108, 112, 114, 116, 118, 128, 130, and one or more of the heating pads 170, 172. For example, the facial wearable device 10 may include a relaxation function, a focus function, and/or a sleep function. In some embodiments, first button assembly 50 may be used to toggle between each of the different present functions. As described above, a short press of first button assembly 50 may activate the first preset (e.g. relaxation), a second short press may activate the second preset (e.g. focus), a third short press may activate the third preset (e.g. sleep), and a fourth short press may deactivate any preset mode of the facial wearable device. First plurality of lights 52 may be configured to indicate the preset selection.

As will be described in more detail below, during operation of one of the preset functions, second button assembly 60 may be used to adjust or modify the functionality of each of the presets. In the illustrative embodiment shown in FIGS. 10-12, second button assembly 60 may include two buttons to individually control two functions. For example, a first button of second button assembly 60 may control the heating level of one or more of heating pads 170, 172, and a second button of second button assembly 60 may control the vibration intensity of one or more of vibration members 140, 142, 144, 146, 148, 150, 152, 154. For example, a short press of the first button of second button assembly may toggle the heating level of one or more of heating pads 170, 172 between low, medium, and high. A short press of the second button of second button assembly may toggle between a low vibration intensity (low voltage provided to each of the plurality of vibration members), a high vibration intensity (high voltage provided to each of the plurality of vibration members), and a wave pattern control of the plurality of one or more vibration members as described above.

In the each of the preset modes, one or more of the plurality of vibration members 140, 142, 144, 146, 148, 150, 152, 154, one or more of the plurality of bladders 104, 108, 112, 114, 116, 118, 128, 130, and one or more of the heating pads 170, 172 may operate concurrently for a predefined treatment time. In some embodiments, the predefined treatment time is approximately fifteen minutes but may be shortened or extended according to the preference of the user. In other embodiments, the treatment time may be, for example, between ten and twenty minutes, between five and twenty-five minutes, or between one and thirty minutes.

When the relaxation preset is activated, one or more of the vibration members 140, 142, 144, 146, 148, 150, 152, 154, one or more of bladders 104, 108, 112, 114, 116, 118, 128, 130, and one or more of heating pads 170, 172 may operate in a default mode. For example, the heating pads 170, 172 may operate at a low heating level (e.g. approximately 37 degrees Celsius), and one or more of the vibration members 140, 142, 144, 146, 148, 150, 152, 154 may operate in a heart control pattern to aid in decreasing the heat rate of the user, as described above and shown in FIGS. 23 and 24. One or more of the bladders 104, 108, 112, 114, 116, 118, 128, 130 may operate in an alternating cycle such that selected bladders inflate at different times. An example relaxation preset function is illustratively shown in FIG. 26.

In the illustrative example shown in FIG. 26, temple bladders 104, 108 may inflate for a first inflation time, stay inflated for a first hold inflation time, and then deflate for a first deflation time, followed by center bladders 128, 130 inflating for a second inflation time, staying inflated for a second hold inflation time, and then deflating for a second deflation time. The cycle may continue between the temple bladders 104, 108, and the center bladders 128, 130. The first and second inflation time may be approximately 5 seconds, the first and second hold inflation time may be 5 seconds, and the first and second deflation time may be 5 seconds. The deflation time may be subdivided into an active deflation time (e.g. 1.5 seconds of the 5 seconds) and a period where the bladders fully deflated (e.g. 3.5 seconds of the 5 seconds). In some embodiments, the amount of time for each of the first and second inflation times, first and second hold inflation times, and first and second deflation times may be shorter or longer than 5 seconds and different from one another. For example, the inflation, hold, and/or deflation times may be 1, 2, 3, 4, 5, 6, 7, 8, 9, or 10 seconds.

At any time during operation of the relaxation preset, the heat level of the one or more heating elements 170, 172 may be changed. As shown in FIG. 26, for example, a first press of the first button second button assembly 60 may change the heat level from low to medium. A second press of the first button of second button assembly 60 may change the heat level from medium to high. A third press of the first button of second button assembly 60 may switch off the heating function. A fourth press of the first button of second button assembly 60 may reactivate the heating function at the low heat level (default). The vibration function may also be changed during operation of the relaxation preset. As shown in FIG. 26, for example, a first press of the second button of second button assembly 60 may switch off the heart rate control function of the vibration members. A second press of the second button of second button assembly 60 may reactivate the heart level control of the vibration members (default).

When a focus preset is activated, one or more of the vibration members 140, 142, 144, 146, 148, 150, 152, 154, one or more of the bladders 104, 108, 112, 114, 116, 118, 128, 130, and one or more of the heating pads 170, 172 may operate in a default mode. For example, the heating pads 170, 172 may operate at a medium heating level (e.g. approximately 40 degrees Celsius), and the one or more vibration members 140, 142, 144, 146, 148, 150, 152, 154 may operate in a wave pattern as described above, and the plurality of bladders 104, 108, 112, 114, 116, 118, 128, 130 may operate in an alternating cycle such that selected bladders inflate at different times. An example focus preset function is illustratively shown in FIG. 27.

In the illustrative example shown in FIG. 27, one or more center bladders may inflate for a first inflation time, stay inflated for a first hold inflation time, and then deflate for a first deflation time. Then one or more eye bladders 112, 114, 116, 118 may inflate for a second inflation time, stay inflated for a second hold inflation time, and then deflate for a second deflation time. Then one or more temple bladders 104, 108 may inflate for a third inflation time, stay inflated for a third hold inflation time, and then deflate for a third deflation time. The cycle may continue between the one or more center bladders 128, 130, the one or more eye bladders 112, 114, 116, 118, and the one or more temple bladders 104, 108 for the selected treatment time. The first, second, and third inflation times may be approximately 4 seconds, the first, second, and third hold inflation times may be approximately 4 seconds, and the first, second, and third deflation times may be approximate 4 seconds. The deflation time may be subdivided into an active deflation time (e.g. 1.5 seconds of the 4 seconds) and a period where the bladders fully deflated (e.g. 2.5 seconds of the 4 seconds). In some embodiments, the amount of time for each of the first, second, and third inflation times, first, second, and third hold inflation times, and first, second, and third deflation times may be shorter or longer than 4 seconds and different from one another. For example, the inflation, hold, and/or deflation times may be 1, 2, 3, 4, 5, 6, 7, 8, 9, or 10 seconds.

At any time during operation of the focus preset, the heat level of the heating elements 170, 172 may be changed. As shown in FIG. 27, for example, a first press of the first button of second button assembly 60 may change the heat level from medium to high. A second press of the first button of second button assembly 60 may switch off the heating function. A third press of the first button of second button assembly 60 may reactivate the heating function at the low heat level. A fourth press of the first button of second button assembly 60 may change the heat level from low to medium (default). The vibration function may also be changed during operation of the focus preset. As shown in FIG. 27, for example, a first press of the second button of second button assembly 60 may change the vibration member operation from the wave pattern to a constant low intensity across all vibration members. A second press of the second button of second button assembly 60 may change the vibration intensity from low to high. A third press of the second button of second button assembly 60 may switch off the vibration function. A fourth press of the second button of second button assembly 60 may reactivate the vibration members in the wave pattern mode (default).

When a sleep preset is activated, one or more of vibration members 140, 142, 144, 146, 148, 150, 152, 154, and one or more of temple bladders 104, 108, may operate in a default mode. One or more of heating pads 170, 172 may not be activated by default upon selection of the sleep preset. For example, one or more of vibration members 140, 142, 144, 146, 148, 150, 152, 154 may operate with low vibration intensity (constant low voltage applied), and one or more of temple bladders 104, 108 may inflate, hold, and deflate in a defined pattern. An example sleep preset function is illustratively shown in FIG. 28.

In the illustrative example shown in FIG. 28, one or more of temple bladders 104, 108 may inflate for a first inflation time, stay inflated for a first hold inflation time, and then deflate for a first deflation time. In the illustrative example, the first inflation time may be approximately 6 seconds, the first hold inflation time may be approximately 6 seconds, and the first deflation time may be approximate 6 seconds. The deflation time may be subdivided into an active deflation time (e.g. 1.5 seconds of the 6 seconds) and a period where the bladders fully deflated (e.g. 4.5 seconds of the 6 seconds). In some embodiments, the amount of time for each of the inflation time, the hold inflation time, and the deflation time may be shorter or longer than 6 seconds and different from one another. For example, the inflation, hold, and/or deflation times may be 1, 2, 3, 4, 5, 6, 7, 8, 9, or 10 seconds.

At any time during operation of the sleep preset, the heat level of one or more heating elements 170, 172 may be changed. As shown in FIG. 28, for example, a first press of the first button of second button assembly 60 may activate the heating elements 170, 172 to a low heat level (e.g. approximately 37 degrees Celsius). A second press of the first button of second button assembly 60 may change the heat level from low to medium. A third press of the first button of second button assembly 60 may change the heat level from medium to high. A fourth press of the first button of second button assembly 60 may switch off the heating function (default). The vibration function may also be changed during operation of the focus preset. As shown in FIG. 28, for example, a first press of the second button of second button assembly 60 may change the vibration intensity from low to high. A second press of the second button of second button assembly 60 may change vibration member operation from a constant high intensity to the wave pattern. A third press of the second button of second button assembly 60 may switch off the vibration function. A fourth press of the second button of second button assembly 60 may reactivate the vibration members at the low vibration intensity level (default).

Embodiments of the present disclosure including sensors may include one or more of the following sensor types: heart rate sensor, an eye motion sensor, a microphone, a blood pressure sensor, an electroencephalogram sensor, a muscle activity sensor, eye motion sensors, blood pressure sensors, heart rate sensors, an electrocardiography sensor, a photoplethysmography sensor, an electroencephalograph sensor, and accelerometer, a pressure sensor, a touch sensor.

It is to be appreciated that the Detailed Description section, and not any other section, is intended to be used to interpret the claims. Other sections can set forth one or more but not all exemplary aspects as contemplated by the inventor(s), and thus, are not intended to limit this disclosure or the appended claims in any way.

While this disclosure describes exemplary aspects for exemplary fields and applications, it should be understood that the disclosure is not limited thereto. Other aspects and modifications thereto are possible, and are within the scope and spirit of this disclosure. For example, and without limiting the generality of this paragraph, aspects are not limited to the software, hardware, firmware, and/or entities illustrated in the figures and/or described herein. Further, aspects (whether or not explicitly described herein) have significant utility to fields and applications beyond the examples described herein.

Aspects have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative aspects can perform functional blocks, steps, operations, methods, etc. using orderings different than those described herein.

References herein to "one aspect," "an aspect," "an example aspect," or similar phrases, indicate that the aspect described can include a particular feature, structure, or characteristic, but every aspect can not necessarily include the particular feature, structure, or characteristic. Moreover, such phrases are not necessarily referring to the same aspect. Further, when a particular feature, structure, or characteristic is described in connection with an aspect, it would be within the knowledge of persons skilled in the relevant art(s) to incorporate such feature, structure, or characteristic into other aspects whether or not explicitly mentioned or described herein. Additionally, some aspects can be described using the expression "coupled" and "connected" along with their derivatives. These terms are not necessarily intended as synonyms for each other. For example, some aspects can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary aspects, but should be defined only in accordance with the following claims and their equivalents.

What is claimed is:

1. A method of providing external stimuli to a user with a facial wearable device, the method comprising:
   coupling the facial wearable device to the user's facial area, the device comprising:
   a heart rate sensor configured to detect heart rate data of the user,
   a first vibrating member disposed in a first portion of the device, and
   a second vibrating member disposed in a second portion of the device that differs from the first portion of the device;

collecting the heart rate data of the user with the heart rate sensor;

pulsating the first vibrating member and the second vibrating member at a first device pulse rate for a first period of time, wherein the first device pulse rate is based on the heart rate data of the user; and pulsating the first vibrating member and the second vibrating member at a second device pulse rate for a second period of time after the first period of time, wherein the second device pulse rate is based on the heart rate data of the user, wherein the first vibrating member and the second vibrating member are paired, wherein the first vibrating member vibrates at a first intensity and the second vibrating member vibrates at a second intensity different from the first intensity, and the paired first vibrating member and the second vibrating member pulsate in a sequential rhythm to mimic a sinus rhythm of a human heartbeat; and wherein vibration of the first vibrating member and the second vibrating member provides the external stimuli as haptic physical feedback to the user to aid the user to achieve a desired heart rate.

2. The method of claim 1, wherein the first and second device pulse rates are between a range of 60 pulses per minute and 24 pulses per minute.

3. The method of claim 1, further comprising operating the device in a relaxation mode, wherein the second device pulse rate is less than the first device pulse rate.

4. The method of claim 1, further comprising operating the device in an energize mode, wherein the second device pulse rate is higher than the first device pulse rate.

5. The method of claim 1, further comprising communicating the heart rate data to a separate user device to enable displaying the heart rate data of the user over the first period of time and the second period of time on the separate user device.

6. The method of claim 1, wherein the device further comprises an axis extending across a width of the device and located at a height halfway between a top edge of the device and a bottom edge of the device, wherein the first portion of the device is disposed above the axis, and the second portion of the device is disposed below the axis.

7. The method of claim 1, wherein the device further comprises a third vibrating member disposed in a third portion of the device, wherein the first portion and the third portion are divided by a central axis, and wherein the third vibrating member pairs with the first vibrating member and vibrates at the first intensity.

8. The method of claim 7, wherein the device further comprises a fourth vibrating member disposed in a fourth portion of the device, wherein the second portion and the fourth portion are divided by a central axis, and wherein the fourth vibrating member pairs with the second vibrating member and vibrates at the second intensity.

9. The method of claim 8, wherein the device further comprises a second axis extending across a width of the device, perpendicular to the central axis, and located at a height halfway between a top edge of the device and a bottom edge of the device, wherein the first portion and the third portion are disposed above the axis, and the second portion and the fourth portion are disposed below the axis.

10. A method of providing external stimuli to a user with a facial wearable device, the method comprising:

coupling the facial wearable device to the user's facial area, the device comprising:

a heart rate sensor configured to detect heart rate data of the user, a first vibrating member disposed in a first portion of the device, and a second vibrating member disposed in a second portion of the device that differs from the first portion of the device;

collecting the heart rate data of the user with the heart rate sensor;

pairing the first vibrating member and the second vibrating member to pulsate sequentially to mimic the sinus rhythm of a human heart beat;

pulsating the first vibrating member and the second vibrating member at a first device pulse rate for a first period of time, wherein the first device pulse rate is based on the heart rate data of the user;

pulsating the first vibrating member and the second vibrating member at a second device pulse rate for a second period of time after the first period of time, wherein the second device pulse rate is based on the heart rate data of the user;

operating the device in an operational mode wherein the first device pulse rate is equal to the lesser of a heart rate of the user or an upper limit pulse rate of the device; and wherein pulsation of the first vibrating member and the second vibrating member provides the external stimuli as haptic physical feedback to the user to aid the user to achieve a desired heart rate.

11. The method of claim 10, wherein in the operational mode, the second device pulse rate is equal to the lesser of a first percentage of the heart rate of the user or the upper limit pulse rate of the device.

12. The method of claim 10, wherein the first and second device pulse rates are between a range of 60 pulses per minute and 24 pulses per minute.

13. The method of claim 10, further comprising operating the device in a relaxation mode, wherein the second device pulse rate is less than the first device pulse rate.

14. The method of claim 10, further comprising operating the device in an energize mode, wherein the second device pulse rate is higher than the first device pulse rate.

15. The method of claim 10, further comprising communicating the heart rate data to a separate user device to enable displaying the heart rate data of the user over the first period of time and the second period of time on the separate user device.

* * * * *

UNITED STATES PATENT AND TRADEMARK OFFICE
CERTIFICATE OF CORRECTION

PATENT NO. : 12,263,312 B2
APPLICATION NO. : 18/484677
DATED : April 1, 2025
INVENTOR(S) : Nazarian et al.

Page 1 of 1

It is certified that error appears in the above-identified patent and that said Letters Patent is hereby corrected as shown below:

In the Claims

In Column 29, Claim 8, Lines 54-55, delete "wherein the fourth vibrating member pairs with the second vibrating member and vibrates at the second intensity." and insert the same on Line 55, as a new continuation point.

In Column 30, Claim 10, Lines 30-31, delete "wherein the second device pulse rate is based on the heart rate data of the user;" and insert the same on Line 29, after "time,", as a continuation point.

Signed and Sealed this
Tenth Day of June, 2025

Coke Morgan Stewart
*Acting Director of the United States Patent and Trademark Office*